United States Patent
Zhang et al.

(10) Patent No.: US 11,737,874 B1
(45) Date of Patent: Aug. 29, 2023

(54) ATRIOVENTRICULAR VALVE CLAMPING DEVICE AND ATRIOVENTRICULAR VALVE CLAMPING SYSTEM

(71) Applicant: HANGZHOU VALGEN MEDTECH CO., LTD., Zhejiang (CN)

(72) Inventors: Tingchao Zhang, Zhejiang (CN); Wei Jiang, Zhejiang (CN); Xianzhang Zheng, Zhejiang (CN); Zehan Zhang, Zhejiang (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 0 days.

(21) Appl. No.: 18/192,964

(22) Filed: Mar. 30, 2023

(30) Foreign Application Priority Data

May 7, 2022 (CN) .......................... 202210488903.3

(51) Int. Cl.
*A61F 2/24* (2006.01)

(52) U.S. Cl.
CPC .............. *A61F 2/2454* (2013.01); *A61F 2/24* (2013.01); *A61F 2/246* (2013.01); *A61F 2/2466* (2013.01)

(58) Field of Classification Search
CPC .......... A61F 2/24; A61F 2/2454; A61F 2/246; A61F 2/2466
See application file for complete search history.

(56) References Cited

U.S. PATENT DOCUMENTS

| | | |
|---|---|---|
| 2007/0118154 A1 | 5/2007 | Crabtree |
| 2010/0121433 A1 | 5/2010 | Bolling et al. |
| 2013/0066342 A1 | 3/2013 | Dell et al. |
| 2016/0287387 A1 | 10/2016 | Wei |
| 2020/0085576 A1 | 3/2020 | Reimer et al. |

FOREIGN PATENT DOCUMENTS

| | | |
|---|---|---|
| CN | 112566590 A | 3/2021 |
| CN | 214104757 U | 9/2021 |
| CN | 215130898 U | 12/2021 |

OTHER PUBLICATIONS

The first office action issued in corresponding CN application No. 202210488903.3 dated Jun. 17, 2022.
Notice of allowance issued in corresponding CN application No. 202210488903.3 dated Jul. 12, 2022.

*Primary Examiner* — William H Matthews
(74) *Attorney, Agent, or Firm* — Hauptman Ham, LLP

(57) ABSTRACT

An atrioventricular valve clamping device and an atrioventricular valve clamping system are provided in the disclosure. The atrioventricular valve clamping device includes a support member, an occluding member, and a clamping member. A direction of a central axis of the occluding member is regarded as a Z-direction, a direction parallel to a width direction of the clamping member and perpendicular to the Z-direction is regarded as a Y-direction, and a direction perpendicular to the Y-direction and the Z-direction is regarded as an X-direction. The support member has a length in the Z-direction. The occluding member is sleeved on the support member in the Z-direction. The clamping member is disposed outside the occluding member and configured to be unfolded or folded relative to the occluding member. The occluding member is resilient and has a three-dimensional shape.

20 Claims, 34 Drawing Sheets

ATRIOVENTRICULAR VALVE CLAMPING DEVICE AND ATRIOVENTRICULAR VALVE CLAMPING SYSTEM

CROSS-REFERENCE TO RELATED APPLICATIONS

This application claims priority under 35 U.S.C. § 119(a) to Chinese Patent Application No. 202210488903.3, filed May 7, 2022, the entire disclosure of which is incorporated herein by reference.

TECHNICAL FIELD

This disclosure relates to the field of interventional medical instrument technologies, and in particular, to an atrioventricular valve clamping device and an atrioventricular valve clamping system.

BACKGROUND

Atrioventricular valves such as a mitral valve and a tricuspid valve are one-way valves. A normal and healthy atrioventricular valve can control a flow of blood from an atrium to a ventricle, and prevent blood from flowing from the ventricle to the atrium. For example, as illustrated in FIG. 1, the mitral valve MV is a one-way valve located between the left atrium LA and the left ventricle LV, which can control a flow of blood from the left atrium LA to the left ventricle LV, and prevent blood from flowing from the left ventricle LV to the left atrium LA. The tricuspid valve TV is a one-way valve located between the right atrium RA and the right ventricle RV, which can control the flow of blood from the right atrium RA to the right ventricle RV, and prevent blood from flowing from the right ventricle RV to the right atrium RA.

The mitral valve includes an anterior leaflet and a posterior leaflet, and the tricuspid valve includes an anterior leaflet, a posterior leaflet, and a septal leaflet. Under normal circumstances, during systole of the left ventricle or the right ventricle, edges of any two adjacent valve leaflets of the mitral valve or the tricuspid valve should be in all coaptation to prevent blood from flowing from the ventricle to the atrium. If adjacent valve leaflets of the mitral valve or the tricuspid valve are in insufficient coaptation, during systole of the left ventricle or the right ventricle, the mitral valve or the tricuspid valve cannot be closed sufficiently, so that a back flow of blood from the ventricle to the atrium emerges, which results in a series of pathological and physiological changes called "mitral valve regurgitation" or "tricuspid valve regurgitation".

Interventional valve clamping operation refers to treatment of regurgitation by implanting valve clamping devices into atrioventricular valves such as the mitral valve and the tricuspid valve, to decrease or eliminate a gap between valve leaflets by pulling two valve leaflets that are in insufficient coaptation toward each other.

An existing valve clamping device is provided with a resilient occluding ball between two clamping arms, adjacent valve leaflets each are clamped between one clamping arm and the occluding ball, a degree of stretching of the valve leaflet by the clamping arm is adjusted by a deformation of the occluding ball, and the gap between valve leaflets is occluded by the occluding ball to reduce regurgitation. However, in the existing valve clamping device, two end portions A and B of the occluding ball that are not clamped by the clamping arms fail to sufficiently fit two adjacent leaflets L, as illustrated in FIG. 2, and thus there are leakage ports C and D in positions near the two end portions for blood regurgitation, which affects regurgitation treatment effect.

It is noted that, compared with mitral valve regurgitation, tricuspid valve regurgitation is mostly caused by dilatation of a tricuspid valve annulus, and a gap between adjacent valve leaflets is relatively large, and the leaflets of the tricuspid valve are more fragile. In order to avoid perforation or tearing caused by excessive stress on the leaflets, the valve clamping device should not clamp the tricuspid valve leaflets too tightly, and accordingly, a force of the clamping arms on the occluding ball should not be excessively large, and a deformation of the occlusion ball is limited. Compared with a situation of clamping the mitral valve leaflets, the two end portions A and B spread portions of the adjacent valve leaflets L in the positions near the two end portions A and B to be further apart, the leakage ports C and D will be larger, and thus there will be more regurgitation through the leakage ports C and D.

SUMMARY

In order to solve or at least partially overcome the above-mentioned technical problems, an atrioventricular valve clamping device and an atrioventricular valve clamping system are provided in the disclosure.

In the first aspect, an atrioventricular valve clamping device is provided. The atrioventricular valve clamping device includes a support member, an occluding member, and a clamping member.

A direction of a central axis of the occluding member is regarded as a Z-direction, a direction parallel to a width direction of the clamping member and perpendicular to the Z-direction is regarded as a Y-direction, and a direction perpendicular to the Y-direction and the Z-direction is regarded as an X-direction.

The support member has a length in the Z-direction, the occluding member is sleeved on the support member in the Z-direction, and the clamping member is disposed outside the occluding member and configured to be unfolded or folded relative to the occluding member.

The occluding member is resilient and has a three-dimensional shape.

The occluding member includes two clamping-supporting portions opposite each other in the X-direction, two end portions opposite each other in the Y-direction, and first transition portions each for transition connection between the clamping-supporting portion and the end portion.

On an X-Y plane, an outer contour of each of the two end portions forms a pointed end extending outward in the Y-direction, and the end portion at least partially extends beyond the clamping member in the Y-direction.

In a second aspect, an atrioventricular valve clamping system is provided. The atrioventricular valve clamping system includes the above-mentioned atrioventricular valve clamping device and a delivery device. The delivery device includes a delivery tube having an axial length and a mandrel movably inserted in the delivery tube. The delivery tube is detachably connected with the support member. The mandrel is configured to drive the clamping member to be unfolded or folded.

In the atrioventricular valve clamping device and the atrioventricular valve clamping system provided in the disclosure, the occluding member includes the two clamping-supporting portions that are opposite to each other in the X-direction and configured to be clamped by the two clamping members, the two end portions opposite each other in the Y-direction, and the first transition portions each for transition connection between the clamping-supporting portion and the end portion. On the X-Y plane, the outer contour of each of the two end portions forms a pointed end extending outward in the Y-direction, and the end portion at least partially extends beyond the clamping member in the Y-direction. The atrioventricular valve clamping device may be implanted to clamp adjacent valve leaflets of the mitral or tricuspid valve that have a gap therebetween, and particularly, when the atrioventricular valve clamping device is applied to the tricuspid valve, a deformation degree of the occluding member may be limited. Nevertheless, compared with the related art, the two end portions of the occluding member have the pointed ends, such that corresponding portions of the adjacent valve leaflets adjacent to the two end portions are easy to conform to and fit the pointed ends to produce coaptation, that is, the two end portions can be sufficiently closely fitted by the adjacent valve leaflets to decrease or even eliminate leakage ports that exist in the positions near two end portions in the related art, so that the two end portions can also effectively occlude regurgitation, improving regurgitation treatment effect of the atrioventricular valve clamping device.

BRIEF DESCRIPTION OF THE DRAWINGS

The accompanying drawings herein, which are incorporated into and form part of the specification, illustrate some implementations of the disclosure and are used to explain principles of the disclosure in conjunction with the specification.

In order to describe the technical solutions in implementations of the disclosure or the related art more clearly, the accompanying drawings required to be used in the implementations or the related art will be simply introduced below. Apparently, those of ordinary skill in the art may further obtain other accompanying drawings according to these accompanying drawings without creative efforts.

DETAILED DESCRIPTION

Figure 1:
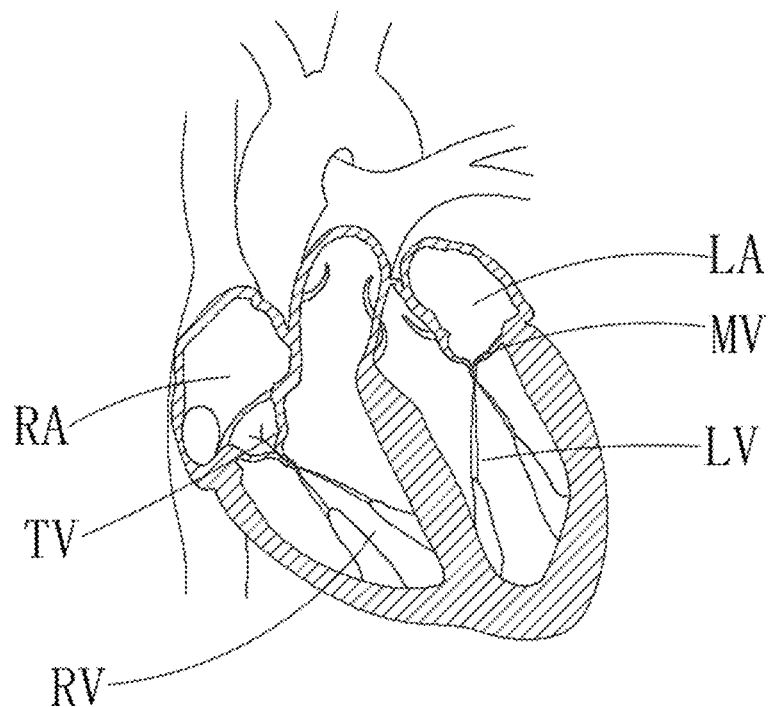
FIG. 1 is a schematic diagram illustrating a mitral valve and a tricuspid valve in a normal state.
Figure 2:
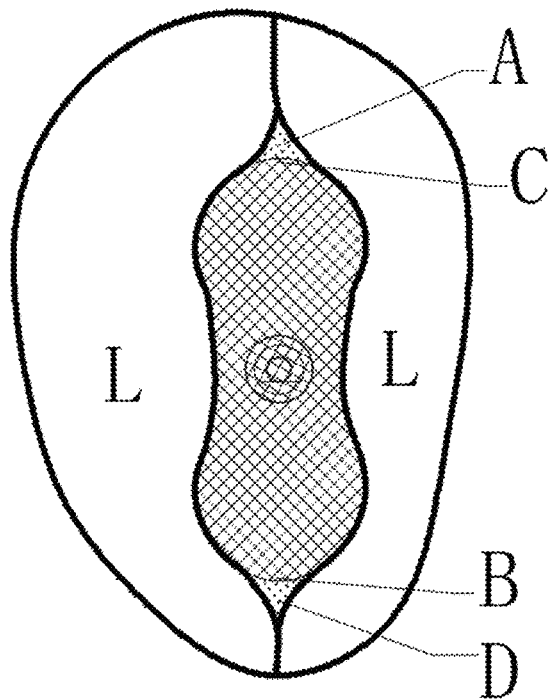
FIG. 2 is a schematic diagram illustrating blood-regurgitation leakage ports existing in positions near two end portions of an occluding ball in the related art.

The technical solutions in implementations of the disclosure are clearly and completely described in the following with reference to the accompanying drawings. Apparently, the described implementations are merely part rather than all of the implementations of the disclosure. All other implementations obtained by those of ordinary skill in the art based on the implementations of the disclosure without creative efforts are within the scope of the disclosure.

In the description of the disclosure, the following should be noted.

Terms such as "on", "under", "in", and "out" which indicate directional relationship or positional relationship are directional relationship or positional relationship based on the accompanying drawings and are only for the convenience of description and simplicity, rather than explicitly or implicitly indicate that apparatuses or components referred to herein must have a certain direction or be configured or operated in a certain direction and therefore cannot be understood as limitation on the disclosure. In addition, terms "first", "second", "third", and the like are only used for description and cannot be understood as explicitly or implicitly indicating relative importance.

When an element is referred to as being "fixed" or "disposed" to another element, the element may be directly connected to the another element or indirectly connected to the another element through one or more connecting elements. When an element is referred to as being "connected" to another element, the element may be directly connected to the other element or connected to the other element through one or more connecting elements.

It is also to be noted that in the field of interventional medical instruments, "proximal end" refers to an end close to an operator, and "distal end" refers to an end farther away from the operator. A direction of the central axis of rotation of objects such as cylinders and tubes is defined as "axial direction". "Circumferential direction" refers to a direction around an axis of objects such as cylinders and tubes (i.e., perpendicular to the axis as well as a radial direction of cross section). "Radial direction" refers to a direction along a diameter or radius. It is noted that, a word "end" in terms such as "proximal end", "distal end", "one end", "other end", "first end", "second end", "initial end", "tail end", "both ends", "free end", "upper end", and "lower end" is not limited to a head-end, an endpoint, or an end face, but also includes a portion extending an axial and/or radial distance from the head-end, the endpoint, or the end face along an element to which the head-end, the endpoint, or the end face belongs. The above definitions are for convenience of illustration only, and should not be construed as limitations on the disclosure.

An atrioventricular valve clamping device provided in the disclosure is configured to repair atrioventricular valves, which include but are not limited to a mitral valve, and a tricuspid valve.

Refer to FIGS. 3-8, the atrioventricular valve clamping device 100 provided in an implementation of the disclosure includes a support member 110, an occluding member 120, and a clamping member 130.

Figure 5:
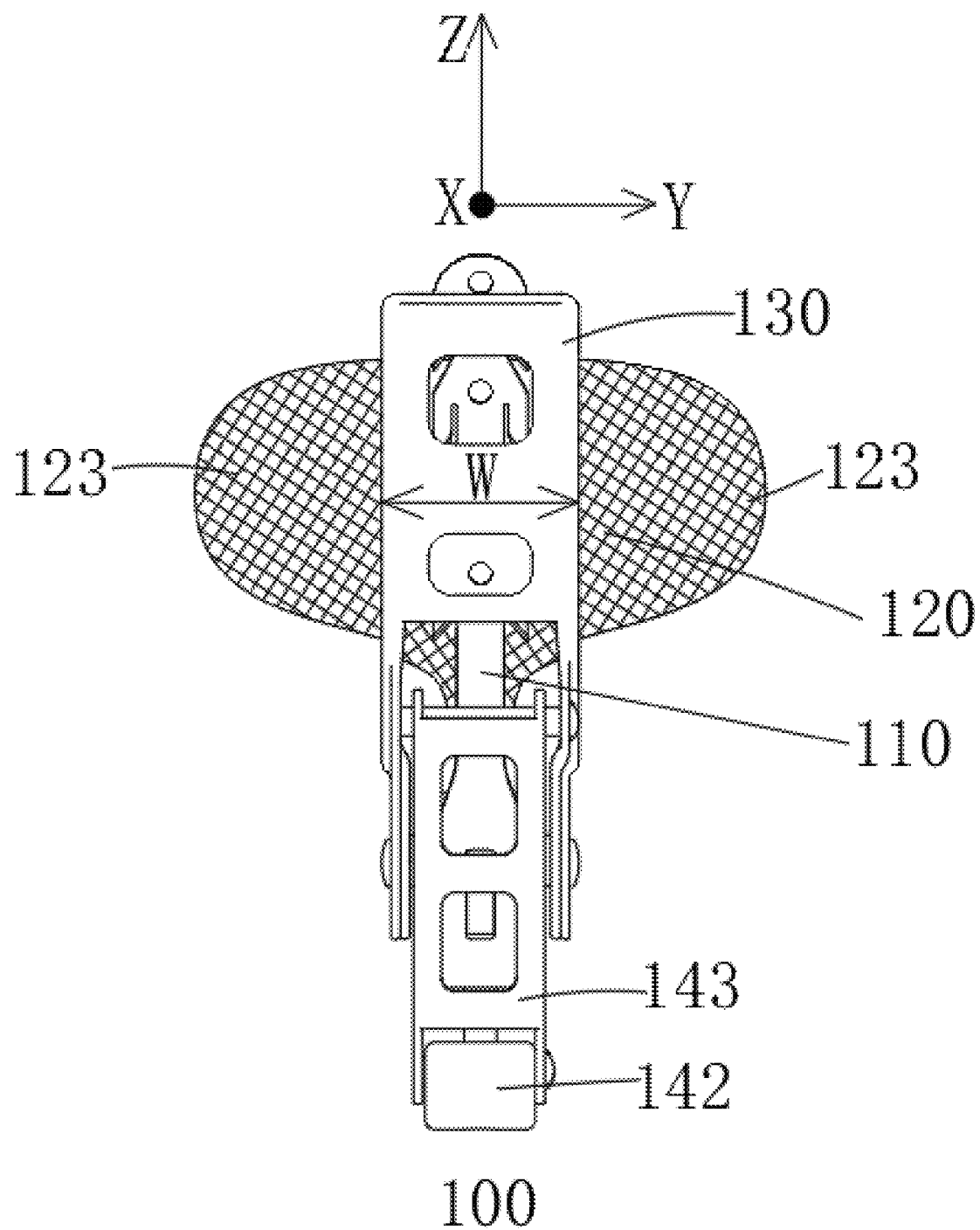
FIG. 5 is a side view of the atrioventricular valve clamping device illustrated in FIG. 3 when the clamping member is in the first folded state.
Figure 6:
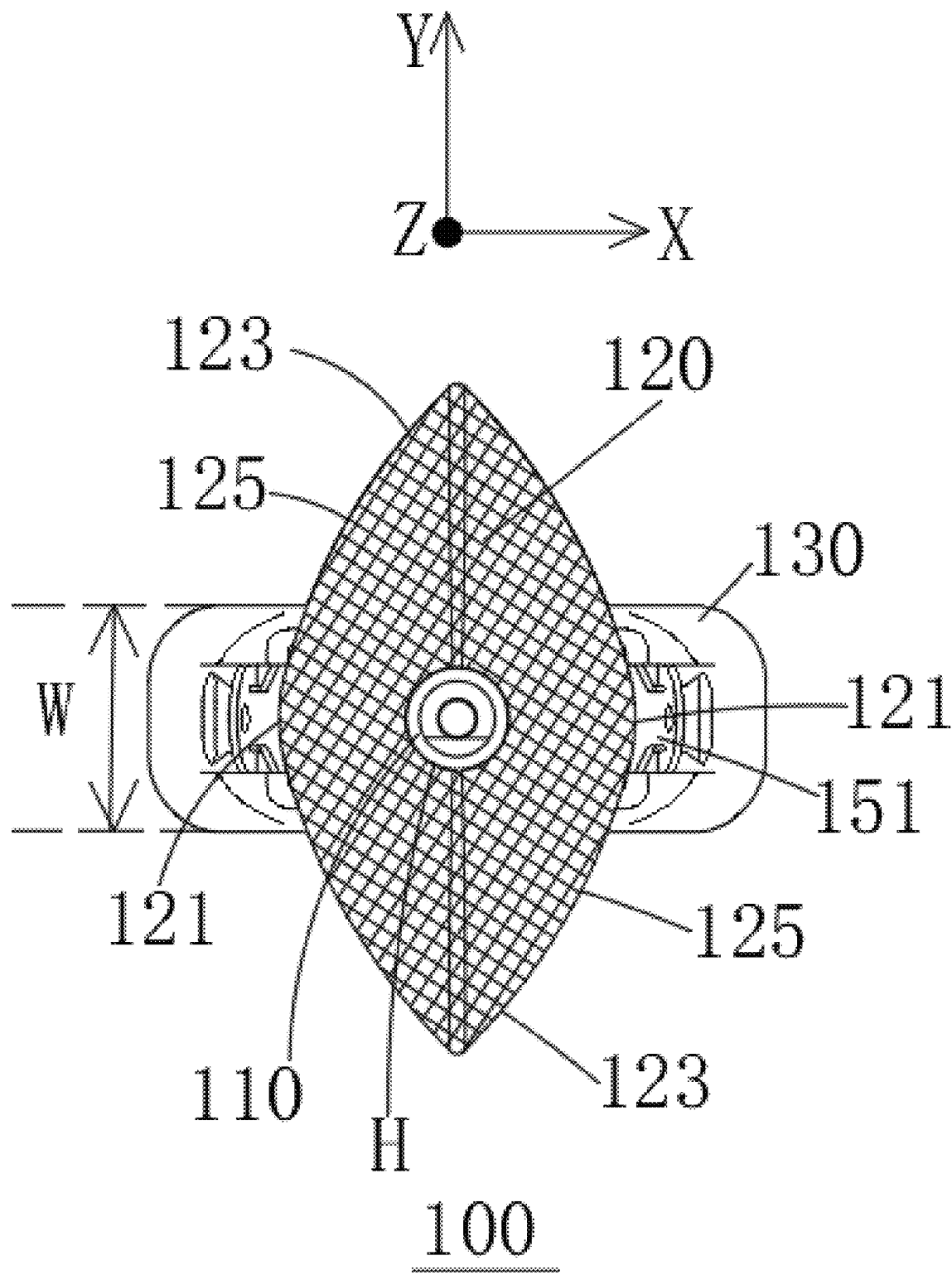
FIG. 6 is a top view of the atrioventricular valve clamping device illustrated in FIG. 3 when the clamping member is in the first folded state.
Figure 7:
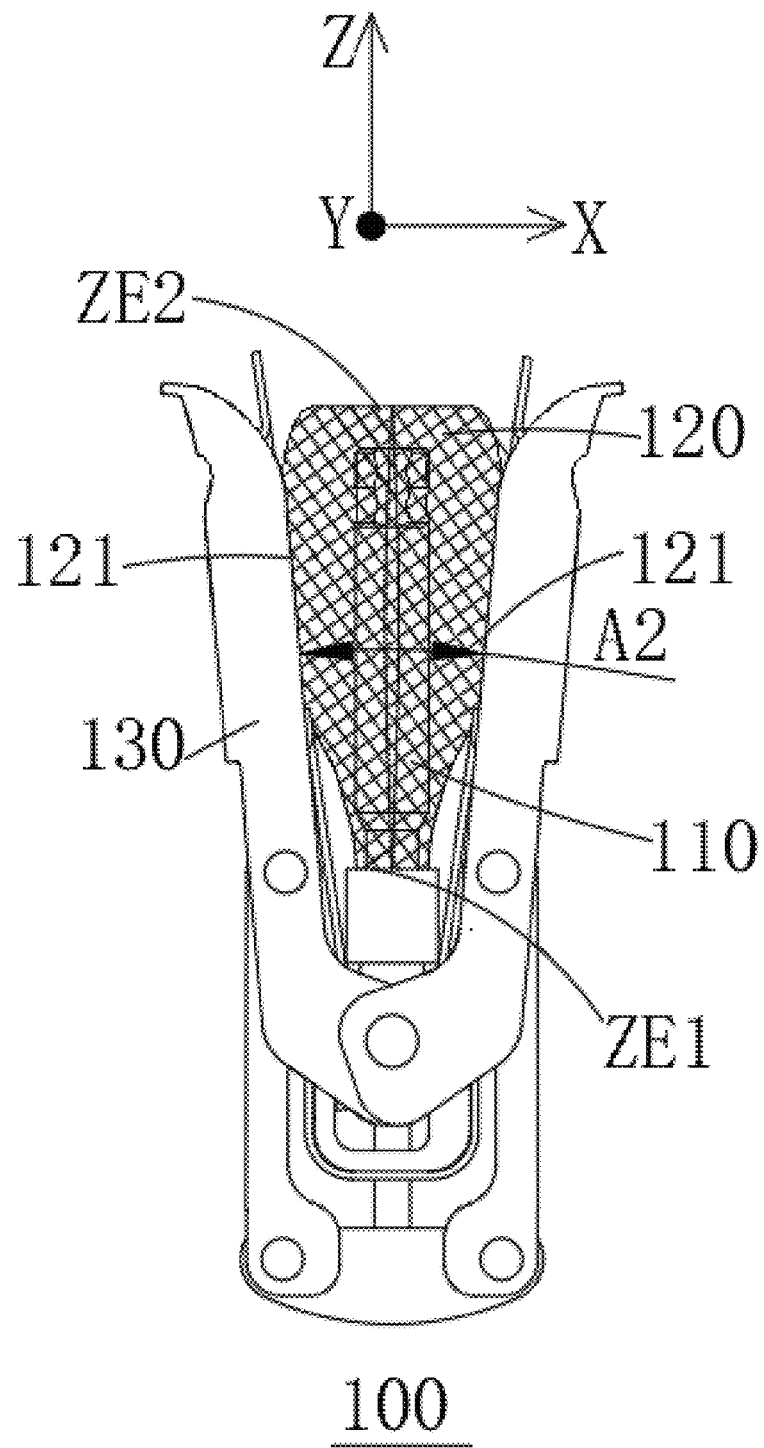
FIG. 7 is a front view of the atrioventricular valve clamping device illustrated in FIG. 3 when the clamping member is in a second folded state.
Figure 8:
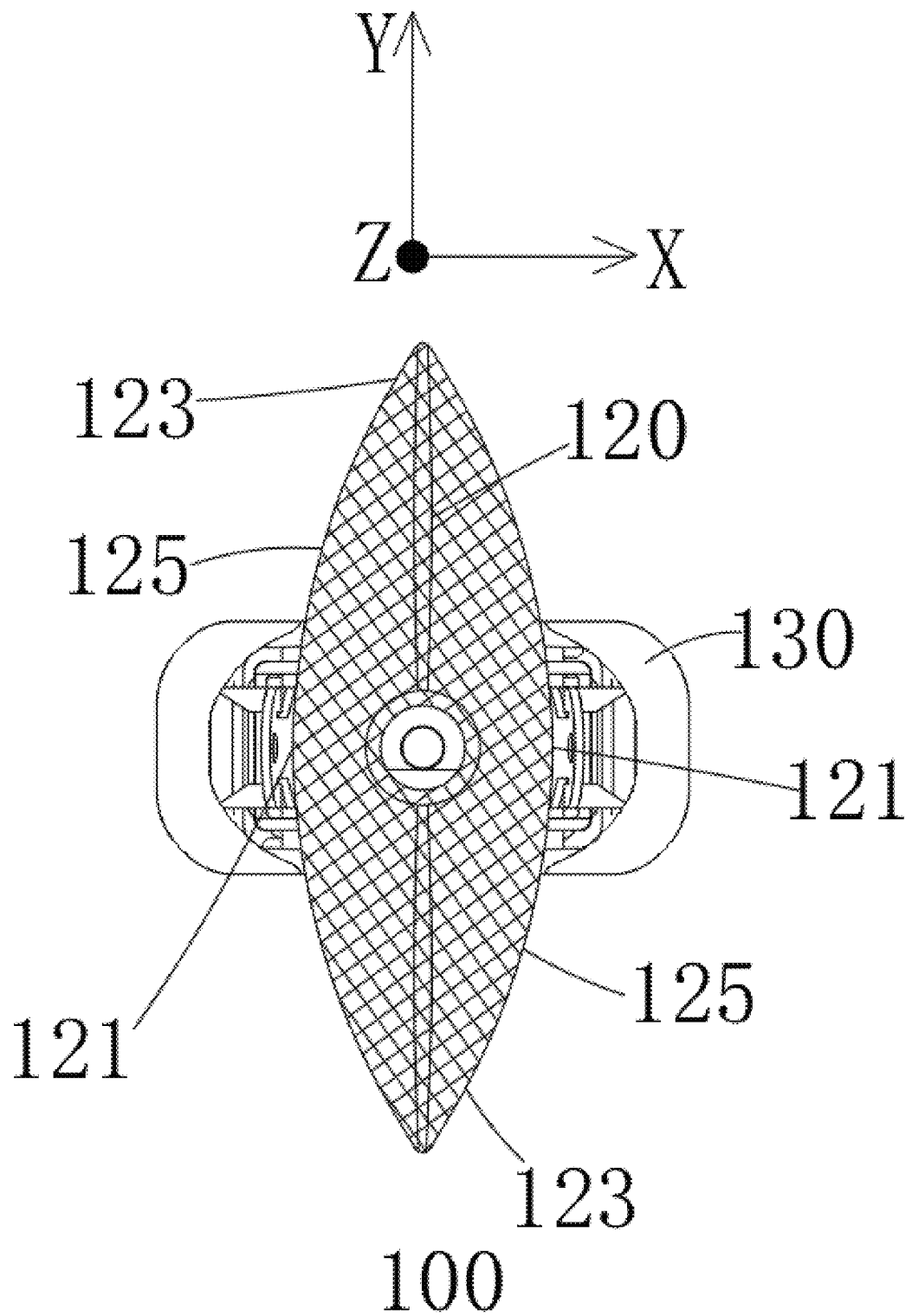
FIG. 8 is a top view of the atrioventricular valve clamping device illustrated in FIG. 3 when the clamping member is in the second folded state.

In combination with FIGS. 9-14, for clarity and convenience of illustration, the following directions are defined. A direction O-O of a central axis of the occluding member 120 (that is, a direction of a central axis of the support member 110) is regarded as a Z-direction, a direction parallel to a direction along the width W (as illustrated in FIG. 5) of the clamping member 130 and perpendicular to the Z-direction is regarded as a Y-direction, and a direction perpendicular to the Y-direction and the Z-direction is regarded as an X-direction. X-Y plane refers to a plane perpendicular to the Z-direction and defined by a straight line extending in the X-direction and a straight line extending in the Y-direction which are intersected with each other. It may be understood that there may be multiple X-Y planes, and the multiple X-Y planes may be arranged in parallel in the Z-direction. X-Z plane refers to a plane perpendicular to the Y-direction and defined by a straight line extending in the X-direction and a straight line extending in the Z-direction which are intersected with each other. It may be understood that there may be multiple X-Z planes, and the multiple X-Z planes may be arranged in parallel in the Y-direction. Y-Z plane refers to a plane perpendicular to the X-direction and defined by a straight line extending in the Y-direction and a straight line extending in the Z-direction which are intersected with each other. It may be understood that there may be multiple Y-Z planes, and the multiple Y-Z planes may be arranged in parallel in the X-direction.

Figure 12:
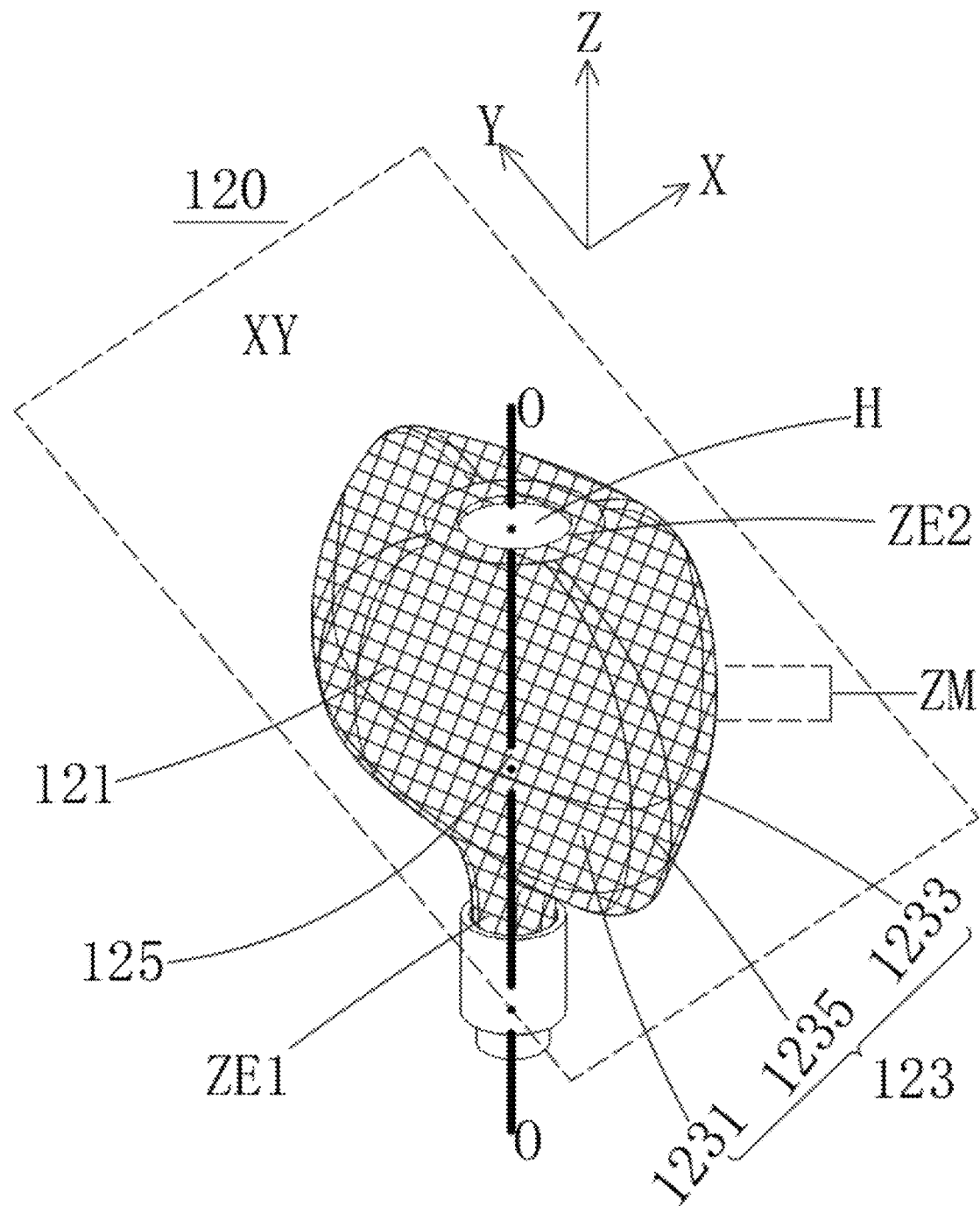
FIGS. 12-14 are respectively schematic perspective structural diagrams of the occluding member in the atrioventricular valve clamping device illustrated in FIG. 3, viewed from different perspective s.
Figure 13:
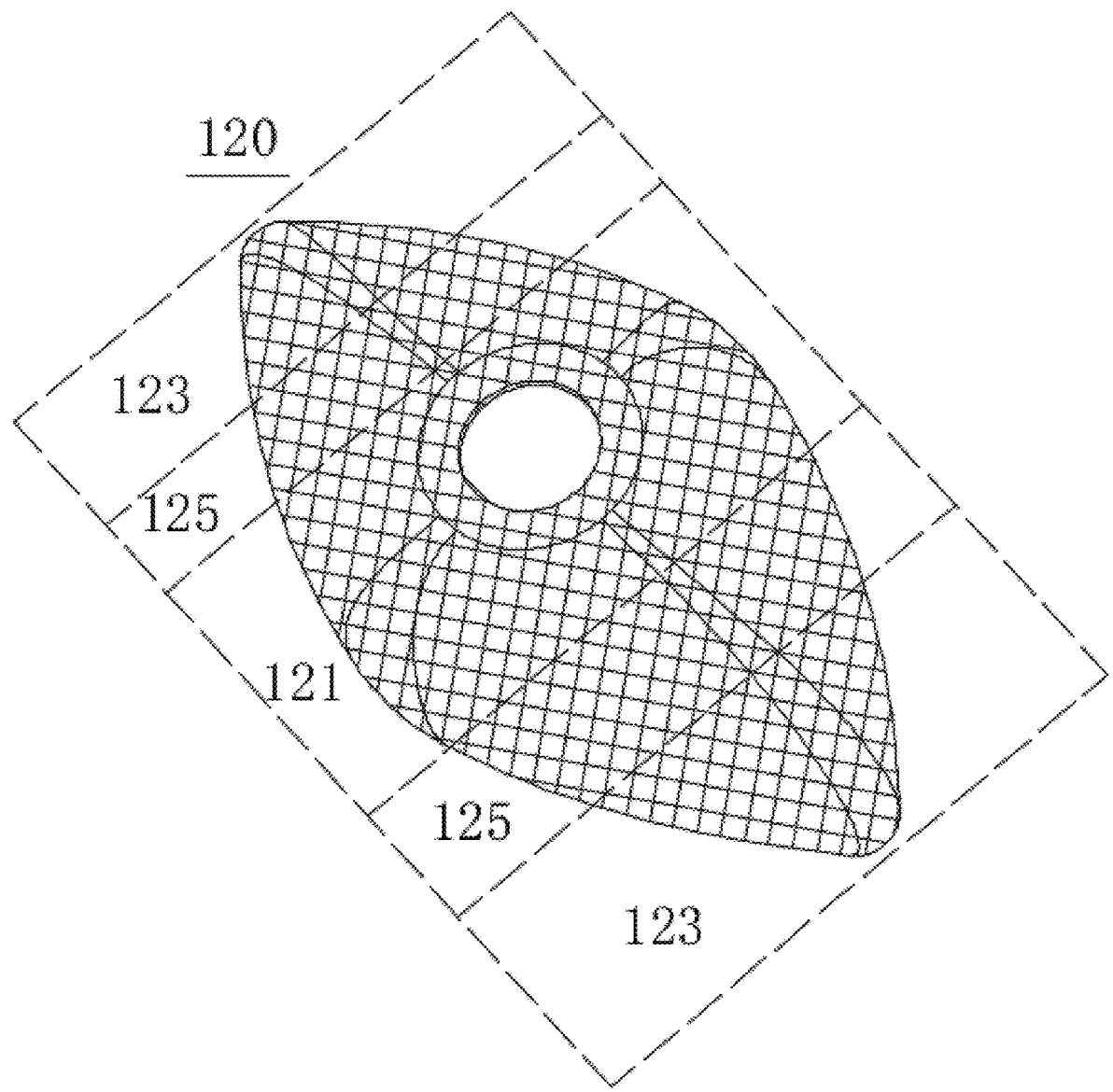
Figure 14:
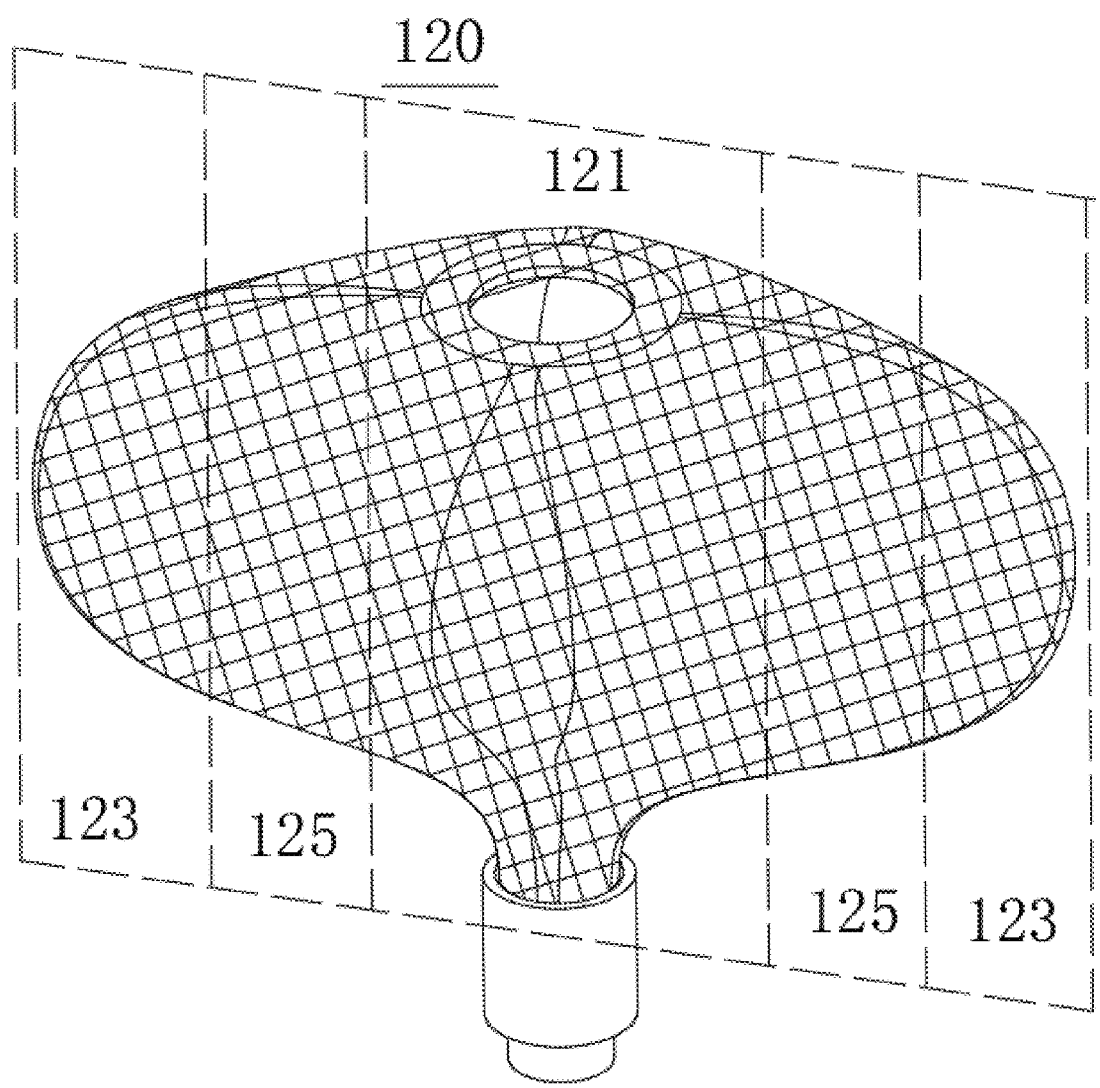
Figure 15:
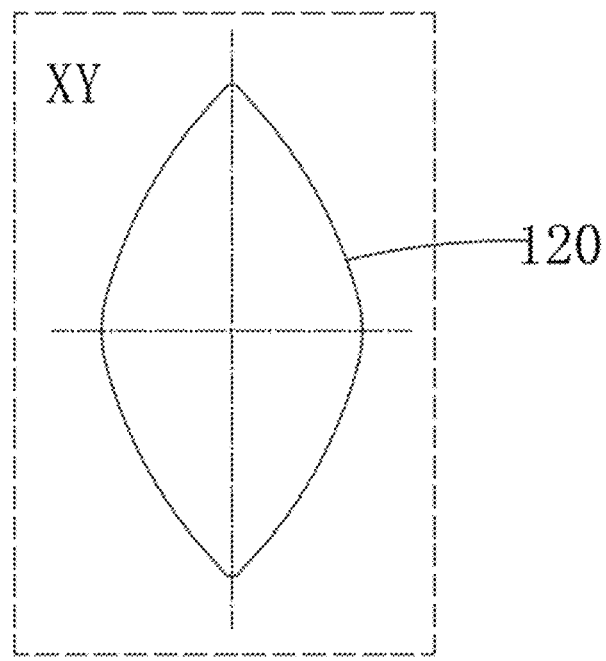
FIG. 15 and FIG. 16 are schematic diagrams illustrating different shapes of an outer contour of the occluding member on an X-Y plane.
Figure 16:
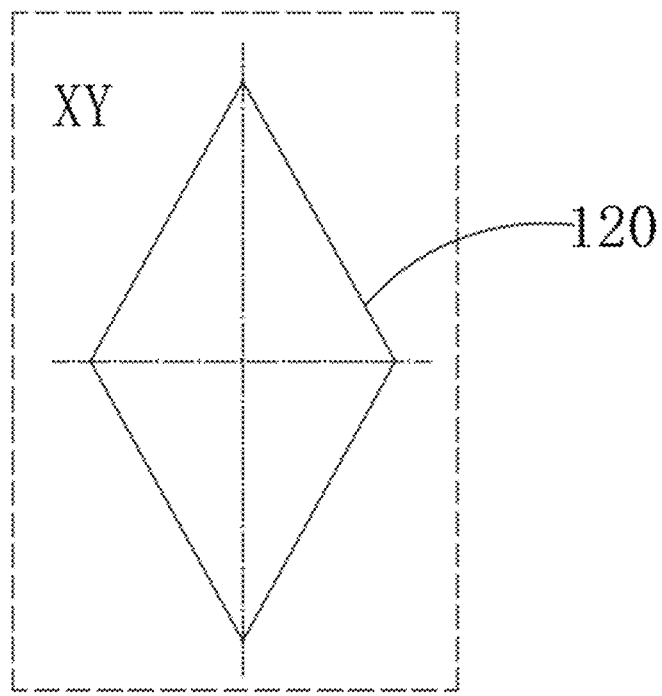

The support member 110 has an axial length (i.e., a Z-direction length). The occluding member 120 is sleeved on the support member 110 in the Z-direction. The clamping member 130 is disposed outside the occluding member 120 and configured to be unfolded or folded relative to the occluding member 120. The occluding member 120 is resilient and has a three-dimensional shape. The occluding member 120 includes two clamping-supporting portions 121 opposite each other in the X-direction, two end portions 123 opposite each other in the Y-direction, and first transition portions 125 each for transition connection between the clamping-supporting portion 121 and the end portion 123. On the X-Y plane (which may be one of the above multiple X-Y planes), an outer contour of each of the two end portions 123 forms a pointed end extending outward in the Y-direction, the end portion 123 at least partially extends beyond the clamping member 123 in the Y-direction. It is noted that, the pointed end is defined relative to the clamping-supporting portion 121 and the first transition portion 125 which are relatively gentle. The pointed end represents that the end portion 123 is pointed or tend to be pointed. The outer contour on the X-Y plane refers to an outline formed at an intersection of the X-Y plane and the occluding member 120 when cutting the occluding member 120 with the X-Y plane, or an outline of a projection of the occluding member 120 on the X-Y plane. For example, as illustrated in FIG. 12 and FIG. 15, on the X-Y plane, the outer contour of the occluding member 120 is in the shape of an olive. As illustrated in FIG. 12 and FIG. 16, on the X-Y plane, the outer contour of the occluding member 120 is in the shape of a rhombus or a substantial rhombus. In other implementations, on the X-Y plane, the outer contour of the occluding member 120 may also be in the shape of a fusiform or the like.

Figure 10:
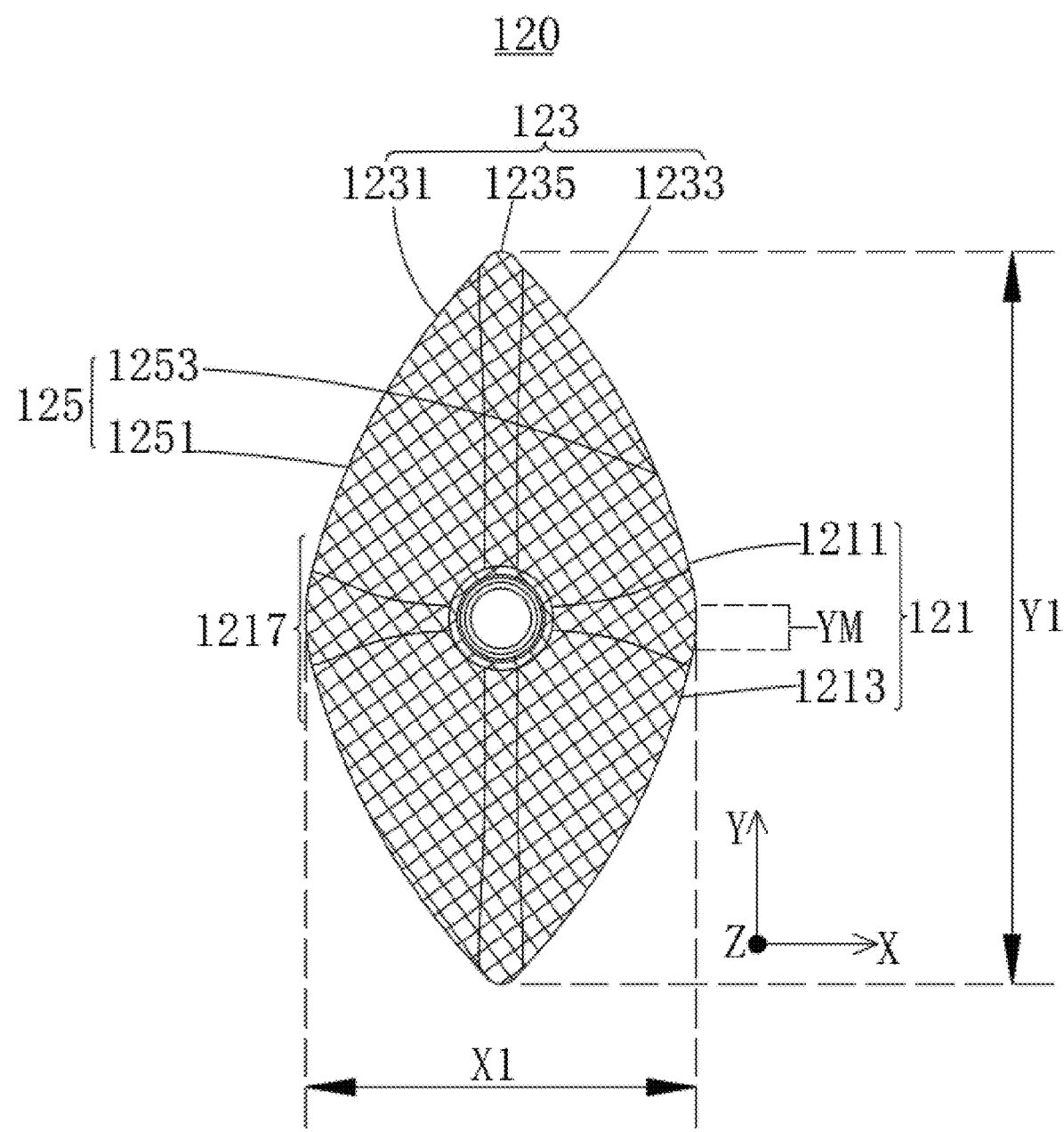

In the implementation, as illustrated in FIGS. 4, 6, 7, 8, 24, and 25, the two clamping-supporting portions 121 cooperate with the clamping member 130 to clamp the valve leaflets. A distance by which the clamping-supporting portion 121 extends in the Y-direction is approximately equal to a width W of the clamping member 130. The clamping-supporting portion 121 may provide an adjustable and adaptive supporting force according to a degree of folding of the clamping member 130. The two end portions 123 are not clamped by the clamping member 130 and exposed to the outside of the clamping member 130 in the Y-direction. A distance by which each of the two end portions 123 extends in the Y-direction may be 0.1 to 2 times the width W of the clamping member 130. The first transition portion 125 is smoothly transitioned and connected between the clamping-supporting portion 121 and the end portion 123. As illustrated in FIG. 10, a maximum value X1 among distances between each two opposite parts of the two clamping-supporting portions 121 (two opposite parts herein refer to two parts of the two clamping-supporting portion 121 on a same straight line in parallel with the X-direction) in the X-direction is less than a maximum value Y1 among distances between each two opposite parts of the two end portions 123 (two opposite parts herein refer to two parts of the two end portions 123 on a same straight line in parallel with the Y-direction) in the Y-direction, and the two end portions 123 are sharper than the two clamping-supporting portions 121. On the X-Y plane, the occluding member 120 has an outer contour in the shape of oval, fusiform, or rhombus, and the outer contour in the shape of oval, fusiform, or rhombus has a short axis in the X-direction and a long axis in the Y-direction.

Further, as illustrated FIGS. 6, 8, 10, and 12, on the X-Y plane, the two clamping-supporting portions 121 have an outer contour substantially in the shape of two opposite arcs that are convex outward, so as to provide reliable and relatively stable support when the clamping member 130 is folded, allowing the clamping member 130 to be folded at a relatively large clamping angle (as indicated by A1 illustrated in FIG. 4) to avoid the valve leaflets from being subjected to excessive stresses. It is noted that, an elastic deformation of the clamping-supporting portion 121 itself also allows the clamping member 130 to be folded at a relatively small clamping angle (as indicated by A2 illustrated in FIG. 7) to provide a relatively large clamping force on the valve leaflets, and thus, the clamping member 130 is adaptable for different types of valve leaflets.

The two end portions 123 have an outer contour forming by a V-shaped pointed-end and an inverted V-shaped pointed-end opposite each other. Specifically, as illustrated in FIG. 10, each of the two clamping-supporting portions 121 includes a first segment 1211 and a second segment 1213 opposite each other in the Y-direction, each of the two end portions 123 includes a third segment 1231 and a fourth segment 1233 opposite each other in the X-direction, and each of the first transition portions 125 includes a fifth segment 1251 and a sixth segment 1253 opposite each other in the X-direction. Distances between each two opposite parts of the two clamping-supporting portions 121 in the X-direction are greater than distances between each two opposite parts of the third segment 1231 and the fourth segment 1233 in the X-direction (two opposite parts herein refer to two parts of the third segment 1231 and the fourth segment 1233 on a same straight line in parallel with the X-direction). Distances between each two opposite parts of the two end portions 123 in the Y-direction are greater than distances between each two opposite parts of the first segment 1211 and the second segment 1213 in the Y-direction (two opposite parts herein refer to two parts of the first segment 1211 and the second segment 1213 on a same straight line in parallel with the Y-direction). Further, in the Y-direction from a Y-direction middle-segment of the occluding member 120 to the end portion 123, the distances between each two opposite parts of the two clamping-supporting portions 121 in the X-direction gradually decrease, the distances between each two opposite parts of the fifth segment 1251 and the sixth segment 1253 in the X-direction (two opposite parts herein refer to two parts of the fifth segment 1251 and the sixth segment 1253 on a same straight line in parallel with the X-direction) gradually decrease, and the distances between each two opposite parts of the third segment 1231 and the fourth segment 1233 in the X-direction gradually decrease. Here, as illustrated in FIGS. 3, 4, 7, 9, and 12, the occluding member 120 includes a first Z-direction end-portion ZE1 and a second Z-direction end-portion ZE2. The outer contour of the occluding member 120 on the X-Y plane gradually increases from the second Z-direction end-portion ZE2 to a Z-direction middle-segment ZM of the occluding member 120 (in a direction indicated by arrow 901 illustrated in FIG. 9). The outer contour of the occluding member 120 on the X-Y plane gradually reduces from the Z-direction middle-segment ZM to the first Z-direction end-portion ZE1 of the occluding member 120 (in a direction indicated by arrow 902 illustrated in FIG. 9). The above arrangement makes the overall shape of the occluding member 120 fluent and smooth, allowing the valve leaflets to conform to the shape of the occluding member 120 to the greatest extent, and to fit against the occluding member 120 with a relatively large area.

As illustrated in FIGS. 6, 8, 7, 10, 12, and 13, the V-shaped pointed-end and the inverted V-shaped pointed-end each include the third segment 1231 and the fourth segment 1233 opposite each other. It is noted that, on the X-Y plane, the V-shaped pointed-end and the inverted V-shaped pointed-end each may be in a sharply angled shape; alternatively, a second transition portion 1235 in a shape of an arc that is convex outward is connected between the third segment 1231 and the fourth segment 1233, and the second transition portion 1235 has a radius ranging from 0.005 mm to 5 mm. If the manufacturing process conditions permits, the smaller a value of the radius, the better the occluding member 120, so that the V-shaped pointed-end and the inverted V-shaped pointed-end each may be more similar to be in a sharply angled shape.

Refer to FIG. 3, FIG. 4, and FIGS. 21-23, the atrioventricular valve clamping device 100 mainly includes two states, that is, an unfolded state of the clamping member 130 and a folded state of the clamping member 130. In the unfolded state, the occluding member 120 is in a free state free from external forces. In the folded state, the clamping member 130 may have various forms with different clamping angles or different clamping forces. Refer to FIGS. 9-14, the occluding member 120 is a three-dimensional mesh structure. In an implementation, the occluding member 120 is a three-dimensional mesh structure that has a shape memory function and is wove with wires or cut from a tube, for example, the occluding member 120 is made of a superelastic material such as nickel-titanium alloy wire, so that under different clamping angles or different clamping forces of the clamping member 130, the occluding member 120 may adapt to gaps between different valve leaflets and generate adaptive deformation, thereby adjusting a degree of stretching of the valve leaflets by the atrioventricular valve clamping device 100. For example, for adjacent valve leaflets of the tricuspid valve that define a large gap therebeween but are thin and fragile (the adjacent valve leaflets may be anterior and posterior leaflets, anterior and septal leaflets, or posterior and septal leaflets of the tricuspid valve), the clamping member 130 may be folded with a relatively large clamping angle (as indicated by A1 illustrated in FIG. 4) to avoid an excessive stress on the valve leaflets and prevent perforation or tearing of the valve leaflets. For adjacent valve leaflets of the mitral valve (i.e., anterior and posterior leaflets of the mitral valve), the clamping member 130 may be folded at a relatively small clamping angle (as indicated by A2 illustrated in FIG. 7) to provide a relatively large clamping force. It is noted that, the three-dimensional mesh structure includes numerous meshes formed by interlacing multiple first wires and multiple second wires, and a shape of each mesh may be but not limited to quadrilateral. In an implementation, the Z-direction middle-segment ZM of the three-dimensional mesh structure (i.e., the occluding member 120) has a greater mesh density than the rest of the three-dimensional mesh structure. The outer contour of the occluding member 120 on the X-Y plane has the largest dimension at the Z-direction middle-segment ZM, and the Z-direction middle-segment ZM has a relatively large mesh density, which makes the valve leaflets fit better with the Z-direction middle-segment ZM, and is beneficial for the Z-direction middle-segment ZM to provide reliable radial support to the valve leaflets.

As illustrated in FIGS. 4-8, FIG. 24, and FIG. 25, in the folded state of the clamping member 130, the valve leaflets are clamped between the clamping member 130 and the occluding member 120 and fit against the occluding member 120 along the outer contour of the occluding member 120, the occluding member 120 occludes the gap between adjacent valve leaflets to prevent blood regurgitation. It is noted that, on the X-Y plane, the outer contour of each of the two end portions 123 of the occluding member 120 forms a pointed-end extending outward in the Y-direction parallel to the direction along the width W of the clamping member 120, and the end portion 123 at least partially extends beyond the clamping member 130 in the Y-direction, and thus when the atrioventricular valve clamping device 100 is implanted to clamp adjacent valve leaflets of the mitral valve MV (refer to FIGS. 7, 9, and 25) or the tricuspid valve (refer to FIGS. 4, 6, and 24) that have a gap therebetween, and particularly, when the atrioventricular valve clamping device 100 is applied to the tricuspid valve TV, a deformation degree of the occluding member 120 may be limited. Nevertheless, compared with the related art, the two end portions 123 of the occluding member 120 have the pointed-ends, such that corresponding portions of the adjacent valve leaflets adjacent to the two end portions 123 are easy to conform to and fit the pointed-ends to produce coaptation, that is, the two end portions 123 can be sufficiently closely fitted by the adjacent valve leaflets to decrease or even eliminate leakage ports that exist in positions near two end portions in the related art, so that the two end portions 123 can also effectively occlude regurgitation, improving regurgitation treatment effect of the atrioventricular valve clamping device 100.

It may be understood that, since the outer contour of the occluding member 120 on the X-Y plane is in the shape of an olive, a fusiform, or a rhombus, etc., when the clamping angle of the clamping member 130 reduces or the clamping force of the clamping member 130 increases, the deformation degree of the occluding member 120 is increased, but the V-shaped pointed-end and the inverted V-shaped pointed-end of the two end portions 123 can always exist and be further sharpened, such that the two end portions 123 can more effectively occlude regurgitation.

In an implementation, the maximum value Y1 among distances between each two opposite parts of the two end portions 123 in the Y-direction may be 1.5 to 4 times the width W of the clamping member 130, and thus the two end portions 123 may be exposed to the outside of the clamping member 130 in the Y-direction to occlude the gap between adjacent valve leaflets, thereby reducing the number of the atrioventricular valve clamping device 100 implanted.

The occluding member 120 is not limited to a three-dimensional mesh structure, but may also be other resilient self-expandable structures, for example, may be a solid structure of silica gel or a porous structure of sponge.

It may be understood that, in other implementations, the occluding member 120 of the three-dimensional mesh structure may be covered with a biocompatible film at an outside and/or an inside of the occluding member 120. On the one hand, the biocompatible film can serve as a flow-blocking film to improve the regurgitation treatment effect and prevent blood from entering the occluding member 120 to form a thrombus, and on the other hand, the biocompatible film can make the atrioventricular valve clamping device 100 more biocompatible. The biocompatible film may be made from, but not limited to, biocompatible polymer such as poly tetra fluoroethylene (PTFE), expanded poly tetra fluoroethylene (EPTFE), polyester, or silicone resin.

Figure 9:
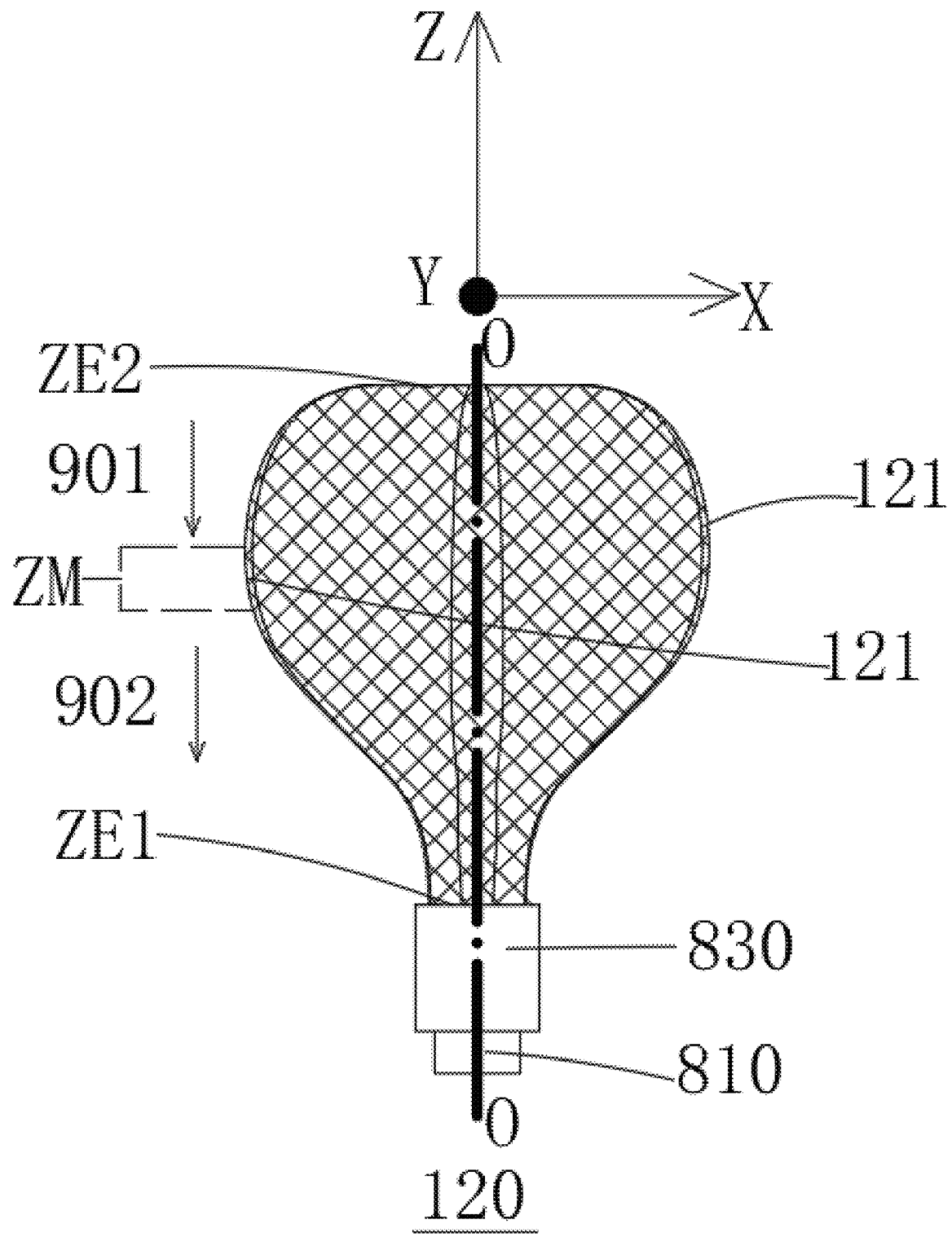
FIGS. 9-11 are respectively a front view, a top view, and a side view of an occluding member in the atrioventricular valve clamping device illustrated in FIG. 3 in a free state.
Figure 11:
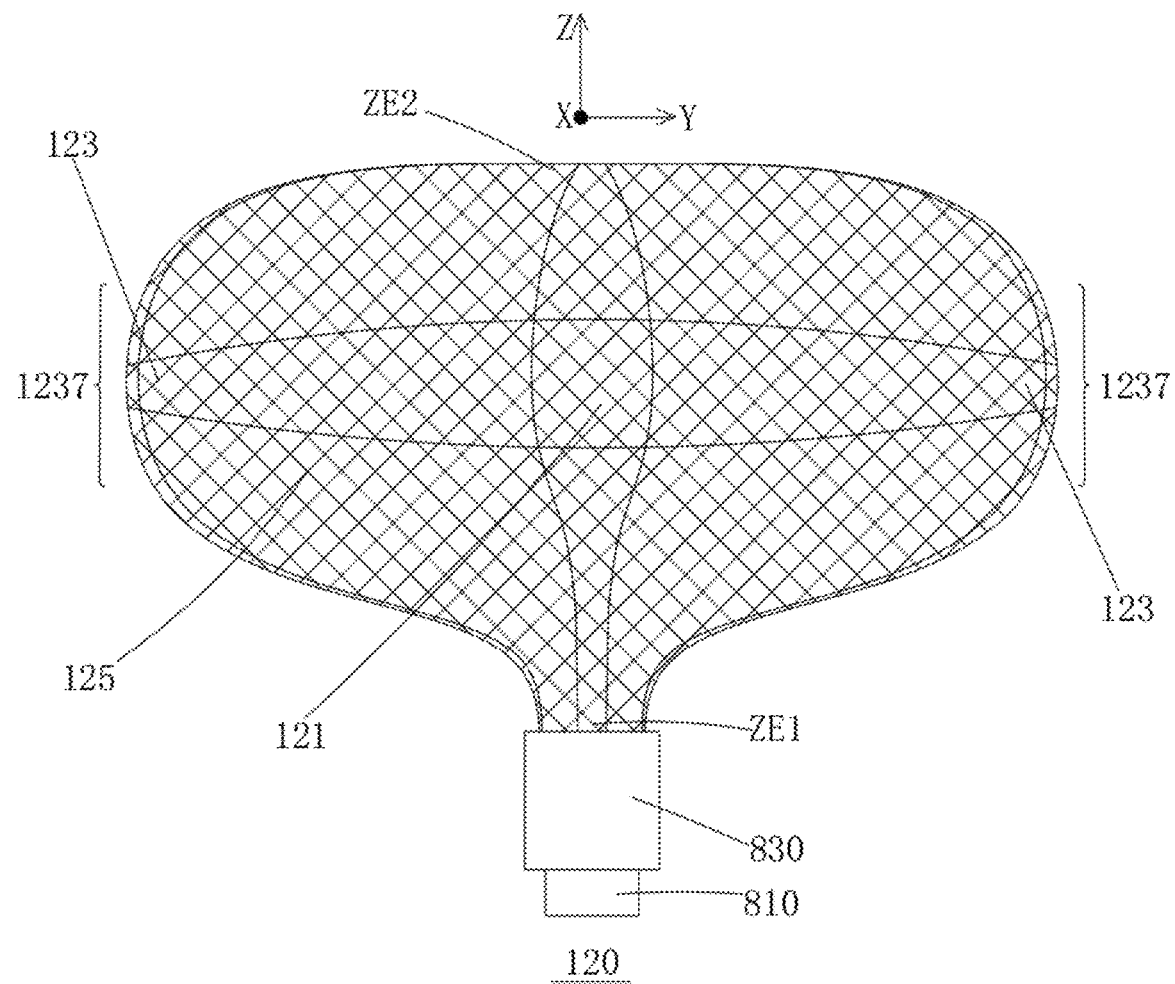

As mentioned above, the occluding member 120 is resilient and has a three-dimensional shape, on the basis that the outer contour of the occluding member 120 on the X-Y plane is in the shape of an olive, a fusiform, or a substantial rhombus, the occluding member 120 further has the following features. As illustrated in FIG. 11, on the Y-Z plane (which may be any one of the above multiple Y-Z planes), the outer contour of the occluding member 120 is substantially in the shape of a capsule, a racetrack, or a water-drop, where the outer contour of the occluding member 120 on the Y-Z plane refers to an outline formed at an intersection of the Y-Z plane and the occluding member 120 when cutting the occluding member 120 with the Y-Z plane, or an outline of a projection of the occluding member 120 on the Y-Z plane. In an example, the outer contour of the two end portions 123 forms two first arc-shaped segments 1237 that are convex outward, and the first arc-shaped segments 1237 serve as a Y-direction edge of the outer contour of the occluding member 120. The above structures can make the occluding member 120 provide sufficient fit length and fit area to the valve leaflets. As illustrated in FIG. 9, on the X-Z plane (which may be any one of the above multiple X-Z planes), the outer contour of the occluding member 120 is substantially in the shape of a water-drop. In an example, an outer contour of the two clamping-supporting portions 121 forms two second arc-shaped segments 1217 that are convex outward, and the two second arc-shaped segments 1217 serve as an X-direction edge of the outer contour of the occluding member 120, where the outer contour of the occluding member 120 on the X-Z plane refers to an outline formed at an intersection of the X-Z plane and the occluding member 120 when cutting the occluding member 120 with the X-Z plane, or an outline of a projection of the occluding member 120 on the X-Z plane. Such arrangement requires both the first Z-direction end-portion ZE1 and the second Z-direction end-portion ZE2 of the occluding member 120 to be closed, that is, both the first Z-direction end-portion ZE1 and the second Z-direction end-portion ZE2 approach the central axis of the occluding member 120. Such arrangement enables the adjacent valve leaflets to gradually approach together along the second arc-shaped segment 1217, which facilitates the valve leaflets following and closely fitting the occluding member 120.

Figure 3:
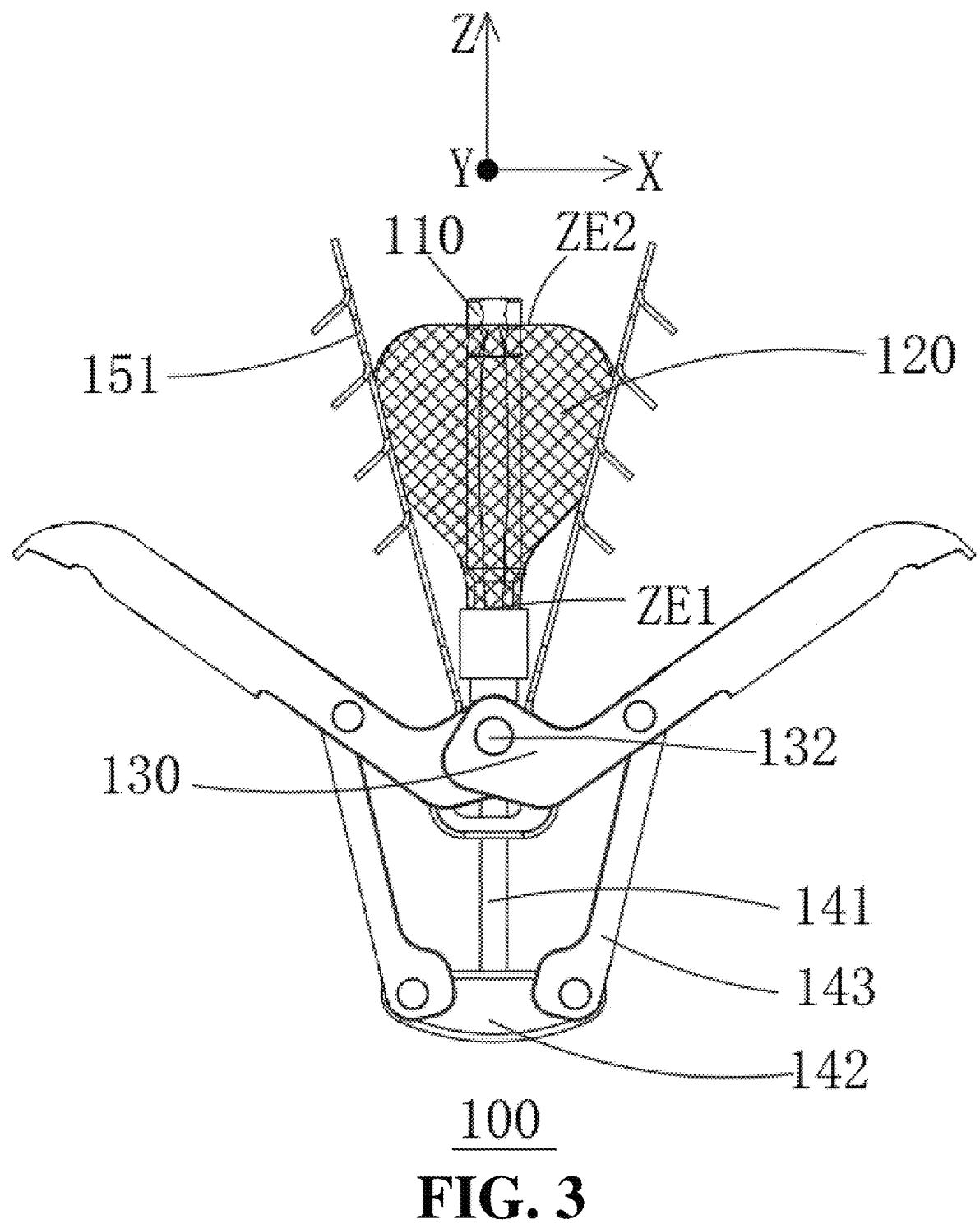
FIG. 3 is a front view of an atrioventricular valve clamping device of an implementation of the disclosure when a clamping member is unfolded.
Figure 4:
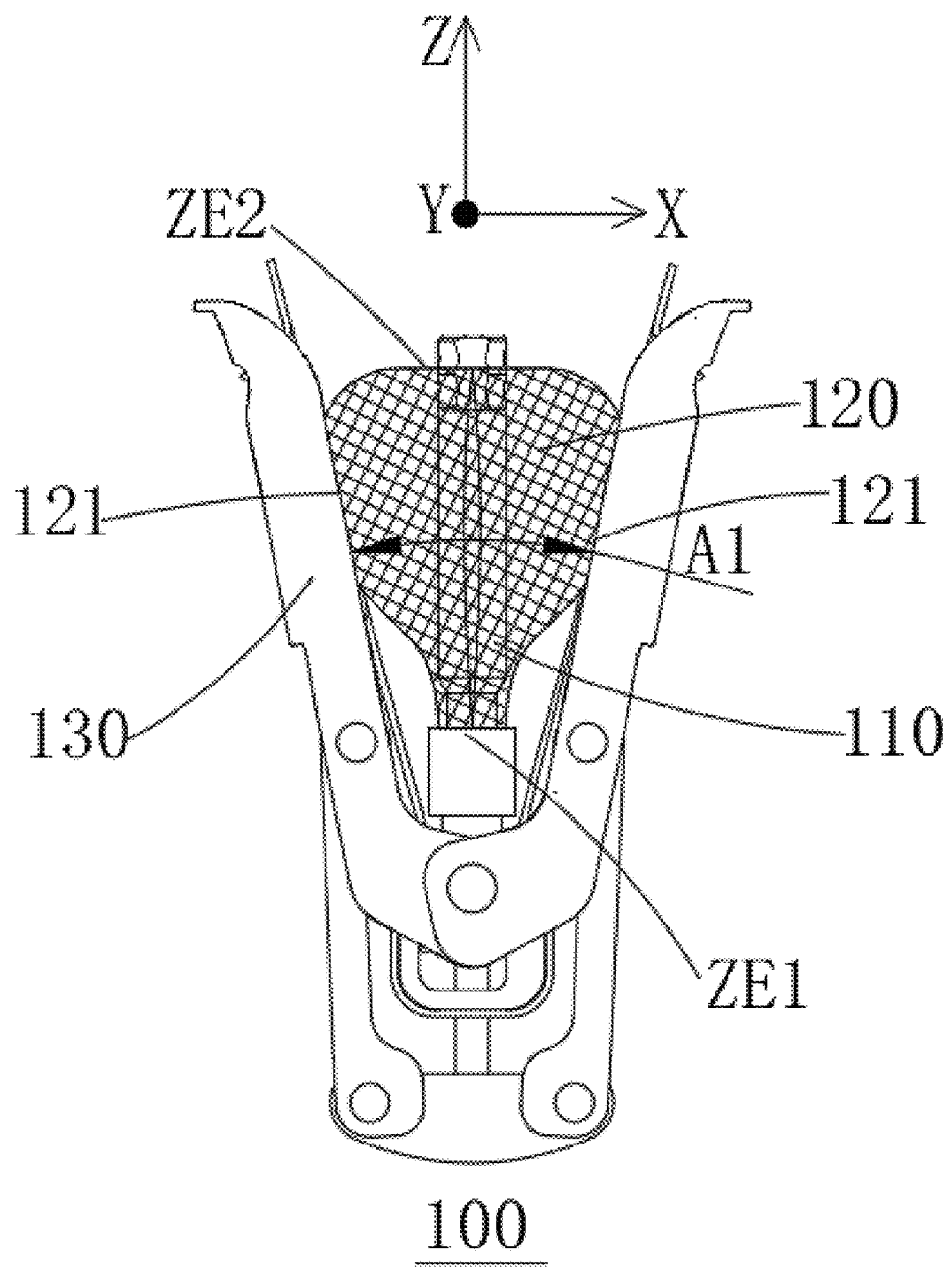
FIG. 4 is a front view of the atrioventricular valve clamping device illustrated in FIG. 3 when the clamping member is in a first folded state.
Figure 17:
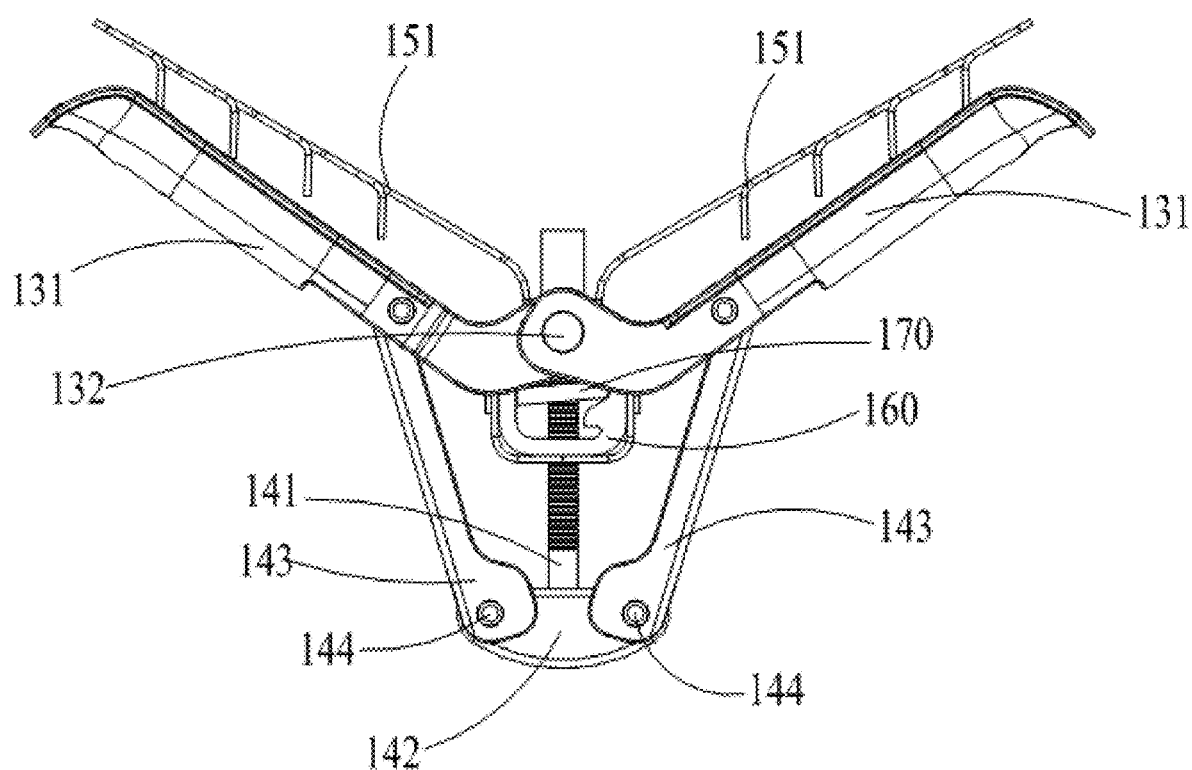
FIG. 17 is a schematic structural diagram of a combination of the clamping member and a driving member in the atrioventricular valve clamping device illustrated in FIG. 3.
Figure 18:
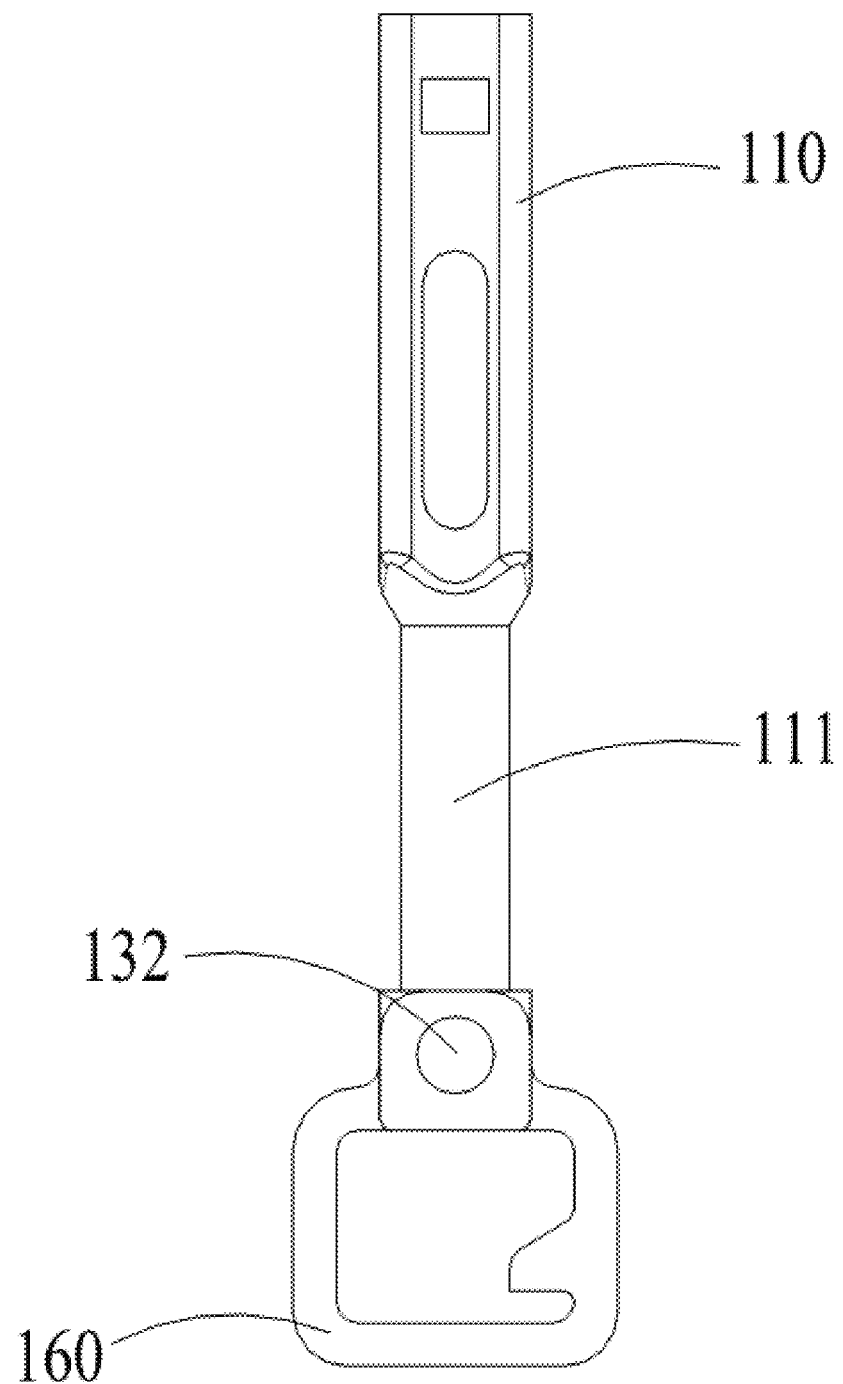
FIG. 18 is a schematic structural diagram illustrating a support member and a base assembled together in the atrioventricular valve clamping device illustrated in FIG. 3.

Specifically, as illustrated in FIG. 18, the support member 110 includes a tube body and a base 160 fixedly connected with the tube body, where both end surfaces of the tube body are axially interpenetrated, and the tube body may be a cylindrical tube body, a square column tube body, or an oblate tube body. In the implementation, the tube body is a cylindrical tube body. As illustrated in FIG. 3 and FIG. 17, the clamping member 130 is rotatably connected with the support member 110 through a pivot point 132, and the clamping member 130 may be radially unfolded or folded about the pivot point 132. As illustrated in FIG. 18, the support member 110 includes a reduced-diameter section 111. Both ends of the reduced-diameter section 111 respectively cooperate with the base 160 and an approximate axial middle of the support member 110 to form steps that are convex radially outward. An axial length (i.e., Z-direction length) of the reduced-diameter section 111 is smaller than a Z-direction length of the entire support member 110. Refer to FIGS. 4, 6, 7, 12 to 14, and 20, the occluding member 120 is hollow. The occluding member 120 is sleeved on the support member 110, and the first Z-direction end-portion ZE1 of the occluding member 120 is closer to the pivot point 132 than the second Z-direction end-portion ZE2 of the occluding member 120. The first Z-direction end-portion ZE1 is fixedly connected (for example, welded) between an inner sleeve 810 and an outer sleeve 830. The second Z-direction end-portion ZE2 defines a through-hole H that is subjected to a bound-off process. The inner sleeve 810 may be movably sleeved on the reduced-diameter section 111, that is, the first end-portion ZE1 may be movably connected with the reduced-diameter section 111 of the support member 110. The second Z-direction end-portion ZE2 may be a free end or movably sleeved on a proximal end of the support member 110 through the through-hole H. It is noted that, the first Z-direction end-portion ZE1 is movably connected with the reduced-diameter section 111 of the support member 110, allowing the first Z-direction end-portion ZE1 to slide in the axial direction (i.e., the Z-direction), and also allowing the first Z-direction end-portion ZE1 to rotate around the axial direction (i.e., the Z-direction). However, when sliding axially, the inner sleeve 810 is restricted by the steps that are convex radially outward, preventing the first Z-direction end-portion ZE1 from being detached from the support member 110.

In the folded state of the atrioventricular valve clamping device 100, that is, when the valves leaflets are clamped between the occluding member 120 and the clamping member 130, since the first Z-direction end-portion ZE1 is movably connected with the reduced-diameter section 111 of the support member 110 within a range less than the Z-direction length of the support member 110, the second Z-direction end-portion ZE2 is a free end or movably sleeved on the proximal end of the support member 110, the occluding member 120 can move in the Z-direction on the reduced-diameter section 111 under clamping of the clamping member 130, allowing the occluding member 120 to significantly deform in the Z-direction to better adapt to shapes or forms of the valve leaflets and increase a fit area between the valve leaflets and the occluding member 120. In addition, the valve leaflets to be clamped can drive the occluding member 120 to rotate around the reduced-diameter section 111, so that in the Y-direction the occluding member 120 conforms to directions of edges of the valve leaflets to be clamped, thereby further improving the occluding effect of the occluding member 120.

It may be understood that, in other implementations, the support member 110 may not include the reduced-diameter section 111. The first Z-direction end-portion ZE1 of the occluding member 120 may be fixedly connected with a distal end of the support member 110 via a fixing member such as a steel sleeve or a sleeve, or directly fixedly connected with the distal end of the support member 110. The second Z-direction end-portion ZE2 is a free end or movably sleeved on the proximal end of the support member 110. As such, in the folded state of the atrioventricular valve clamping device 100, that is, when the valve leaflets are clamped between the occluding member 120 and the clamping member 130, the second Z-direction end-portion ZE2 may move toward the proximal end in the Z-direction, still allowing the occluding member 120 to significantly deform in the Z-direction, to better adapt to the shapes of the valve leaflets and increase the fit area between the valve leaflets and the occluding member 120.

Refer to FIG. 17, the clamping member 130 includes two clamping arms 131 arranged symmetrically with respect to the occluding member 120. It is noted that, there are generally two valve leaflets for clamping repair, which may be the anterior and posterior leaflets of the mitral valve, or the anterior and posterior leaflets, the anterior and septal leaflets, or the posterior and septal leaflets of the tricuspid valve.

In the implementation, the atrioventricular valve clamping device 100 also includes a driving member connected with the clamping member 130, and the driving member is configured to drive the clamping member 130 to unfold or fold relative to the occluding member 120. Specifically, the driving member is connected with each clamping arm 131 to drive each clamping arm 131 to rotate around the occluding member 120, so that the clamping arm 131 moves toward or away from the occluding member 120. In a delivery state, the driving member drives the clamping arms 131 to fold around the occluding member 120, thereby reducing an outer diameter of the atrioventricular valve clamping device 100 and facilitating delivery. After the atrioventricular valve clamping device 100 is deployed in the heart, the driving member drives the clamping arms 131 to clamp the valve leaflets between the clamping arms 131 and the occluding member 120 to realize the valve leaflets clamping.

In an implementation of the implementation, the atrioventricular valve clamping device 100 also includes a gripping member. The gripping member includes two gripping arms 151 arranged symmetrically with respect to the occluding member 120. The gripping member (e.g., the gripping arms 151) is disposed between the clamping member 130 (e.g., the clamping arms 131) and the occluding member 120. The gripping member is configured to be unfolded to be away from the occluding member 120 or configured to be folded to approach the occluding member 120. The gripping arms 151 and the clamping arms 131 cooperatively realize valve leaflet capturing function.

In the delivery state, the gripping member is at least partially received in a space defined by an inner surface of the clamping member 130, that is, the gripping arms 151 are at least partially received in the space defined by the inner surface of the clamping arm 131, thereby reducing the outer diameter of the atrioventricular valve clamping device 100, and facilitating delivery. After the valve leaflets are captured by the clamping arms 131 and the gripping arms 151, the gripping arm 151 presses the valve leaflet into the space defined by the inner surface of the clamping arm 131, which can increase a contact area between the clamping arm 131 and the valve leaflet and increase the clamping force on the valve leaflet.

The base 160 is fixedly connected with a distal end of the reduced-diameter section 111, and each clamping arm 131 is rotatably connected with the base 160. The clamping arms 131 are connected together on the base 160 via a pivot, and the pivot constitutes the pivot point 132. The second end-portion ZE2 of the occluding member 120 is spaced apart from the base 160 in the Z-direction. When driven by the driving member, the clamping arms 131 cooperate with each other to unfold and fold around the occluding member 120 about the pivot point 132 that serves as a rotation center.

In the implementation, the driving member includes a driving shaft 141, a connecting base 142, and two connecting rods 143. Each connecting rod 143 has one end rotatably connected with the clamping member 130 and the other end rotatably connected with the connecting base 142. The driving shaft 141 has one end fixedly connected with the connecting base 142 and the other end movably inserted into the base 160. Specifically, the one end of each connecting rod 143 is rotatably connected with the clamping arm 131, and the other end of each connecting rod 143 is rotatably connected with the connecting base 142 via a pivot 144, that is, each of the two clamping arm 131 is rotatably connected to the connecting base 142 via the connecting rod 143 at a corresponding side. The driving shaft 141 movably penetrates the base 160. When sliding relative to the base 160 in the Z-direction, the driving shaft 141 drives the connecting rods 143 to rotate and drives the two clamping arms 131 to unfold or fold about the pivot point 132 that serves as the rotation center.

Specifically, the connecting rods 143 are arranged in one-to-one correspondence with the clamping arms 131. The one end of the connecting rod 143 is rotatably connected with the connecting base 142 via the pivot 144 such as a pin, and the other end of the connecting rod 143 is rotatably connected with the corresponding clamping arm 131 via a pivot such as a pin. Each clamping arm 131 is rotatably connected with the base 160 via a pivot such as a pin. When moving toward a distal end relative to the base 160 in the Z-direction, the driving shaft 141 drives the connecting rods 143 to move, and the clamping arms 131 rotate around the pivot point 132 and unfold relative to the base 160 under pulling of the connecting rods 143. When the driving shaft 141 moves toward a proximal end relative to the base 160 in the axial direction, the connecting rods 143 push the clamping arms 131 to rotate around the pivot point 132 to fold relative to the base 160. The connecting base 142 may be in any shape such as a hemisphere, a spherical cap, or a bullet, so that it is easy to deliver the atrioventricular valve clamping device 100 in a body. The driving shaft 141 and the connecting base 142 may be of an integral structure or a non-integrated structure. In order to ensure safety after implantation, the driving shaft 141 and the connecting base 142 are made from biocompatible materials such as polyester, silicone resin, stainless steel, cobalt alloy, cobalt-chromium alloy, or titanium alloy, preferably stainless steel or cobalt-chromium alloy with higher hardness.

Refer to FIG. 17, the atrioventricular valve clamping device 100 further includes a locking portion 170 disposed in the base 160. The locking portion 170 is configured to restrict a relative movement between the driving shaft 141 and the base 160. In the delivery state, the locking portion 170 restricts the relative movement between the driving shaft 141 and the base 160, thereby ensuring that the clamping members 130 maintain in the folded state relative to the occluding member 120 and the support member 110, avoiding accidental unfolding of the clamping member 130. After reaching the position near the tricuspid valve or the mitral valve, the restriction on the driving shaft 141 exerted by the locking portion 170 is removed, and then the clamping members 130 may be driven by the driving member to unfold relative to the occluding member 120 and the support member 110 and support the valve leaflets. After the valve leaflets are clamped, the locking portion 170 restricts the relative movement between the driving shaft 141 and the base 160 again, so as to maintain a clamped state of the valve leaflets. The locking portion may be of any existing suitable structure, which is not described herein.

Figure 19:
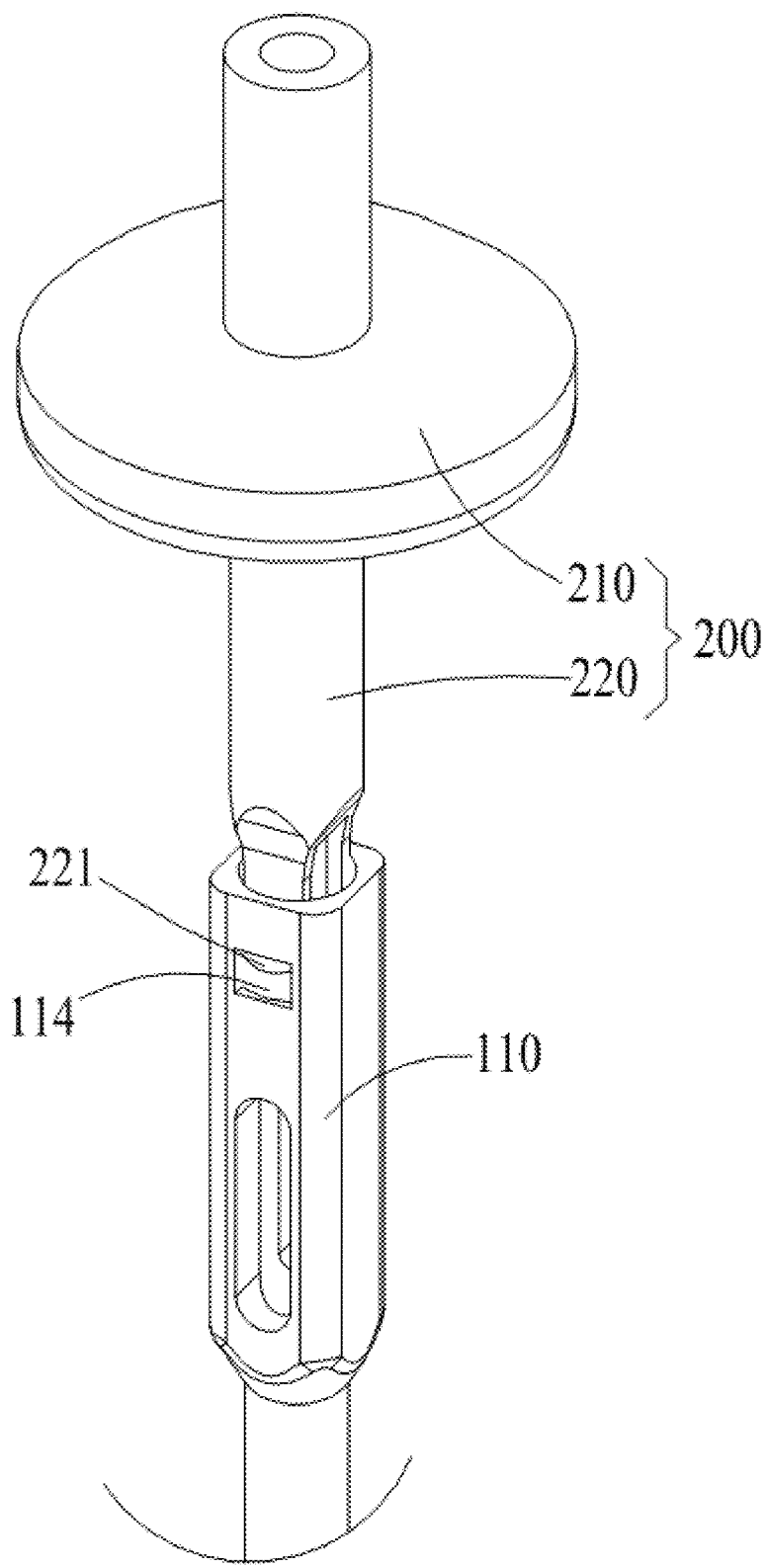
FIG. 19 is a schematic structural diagram of the support member in the atrioventricular valve clamping device illustrated in FIG. 3 and a delivery device assembled together.
Figure 20:
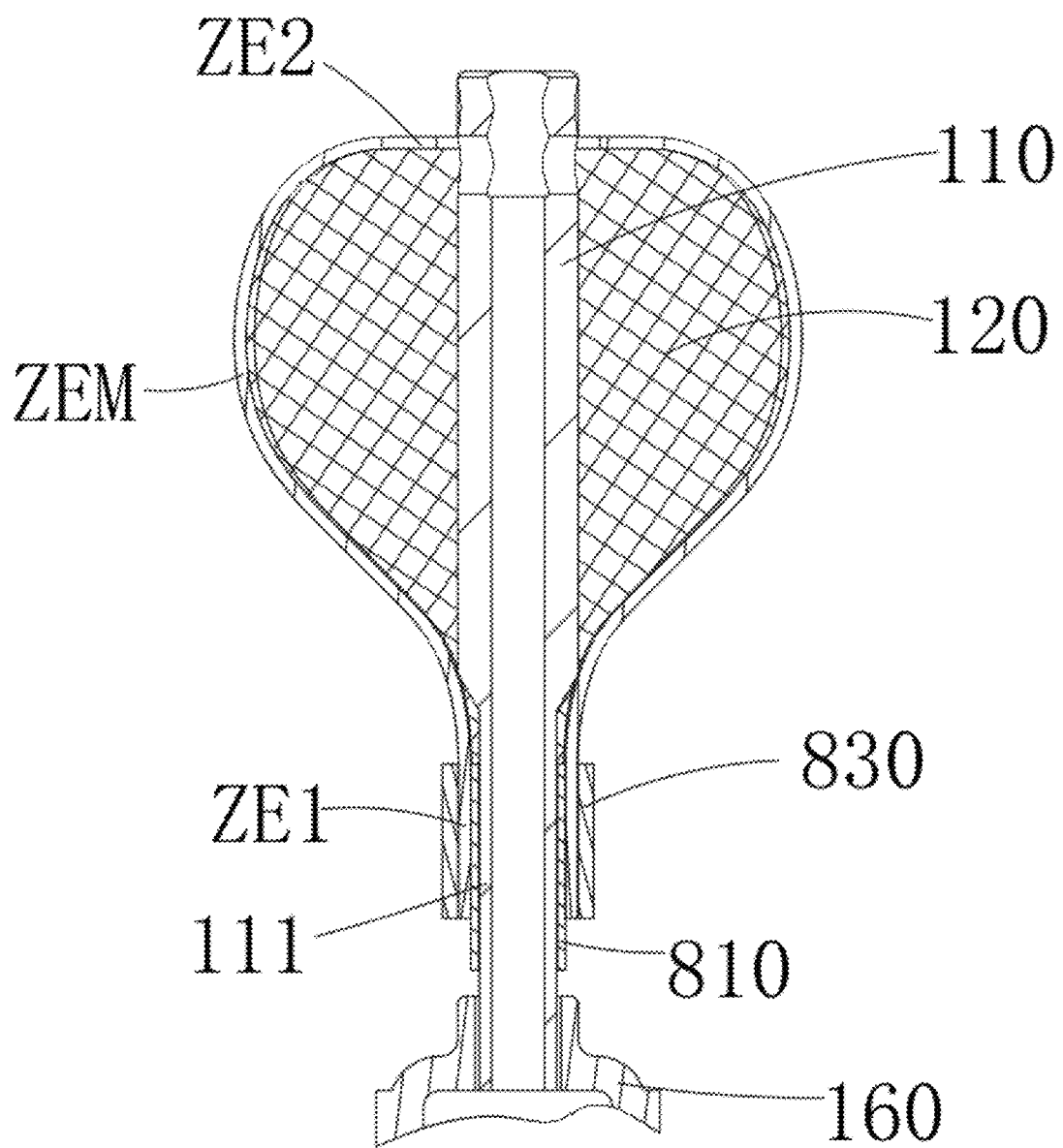
FIG. 20 is a schematic cross-sectional view of an assembly of the support member and the occluding member in the atrioventricular valve clamping device illustrated in FIG. 3.
Figure 21:
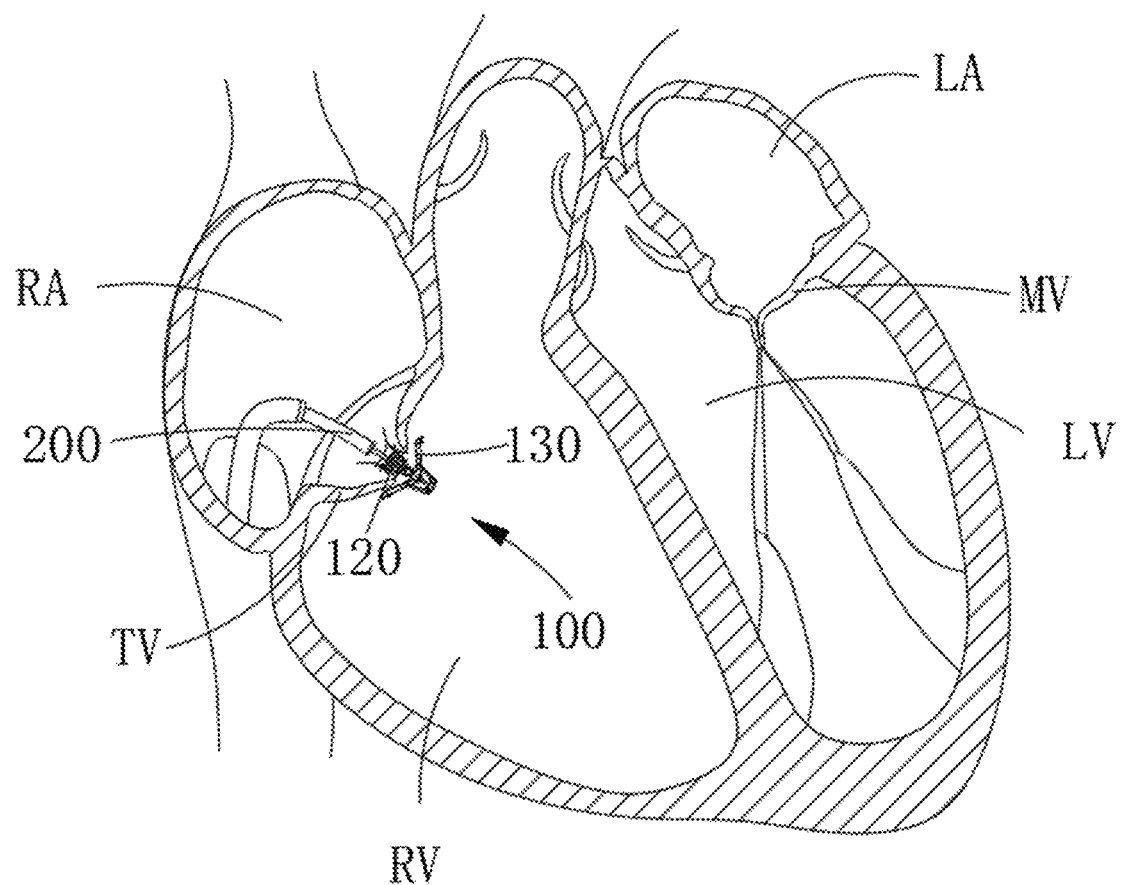
FIGS. 21-23 illustrate a process of repairing adjacent valve leaflets of a tricuspid valve by the atrioventricular valve clamping device illustrated in FIG. 3.
Figure 22:
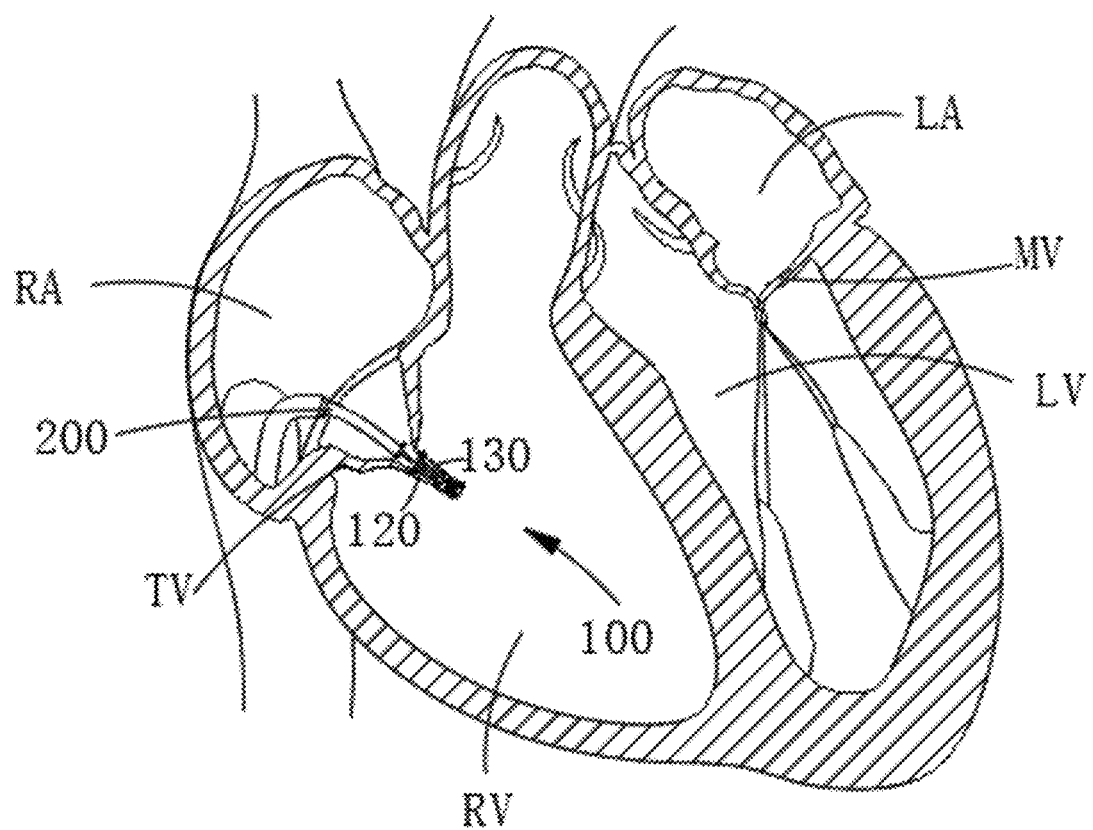

Refer to FIGS. 17-19, and in combination with FIGS. 3-8, a valve clamping system is further provided in the disclosure. The valve clamping system includes the above-mentioned atrioventricular valve clamping device 100 and a delivery device 200. The delivery device 200 includes a delivery tube 210 having an axial length and a mandrel (not illustrated) movably inserted in the delivery tube 210. The delivery tube 210 is detachably connected with the support member 110. The mandrel is detachably connected with the driving member and is configured to drive the clamping member 130 to be unfolded or folded. The support member 110 also defines a penetrating passage extending along the axial direction (i.e., the Z-direction) and being a through-hole, to cooperate with the driving member and the delivery device 200. The support member 110 is provided with at least two snap-fitting openings 114 on a tube wall of the tube body of the support member 110 for detachable connection with the delivery device 200. For example, the delivery device 200 is provided with snap-fitting protrusions 221. After the snap-fitting protrusions 221 are snapped into the snap-fitting openings 114, the delivery device 200 is engaged with the support member 110, and the atrioventricular valve clamping device 100 may be delivered. When the snap-fitting protrusions 221 are detached from the snap-fitting openings 114, the delivery device 200 is detached from the atrioventricular valve clamping device 100. It is understood that, a structure of the support member 110 herein is only used as an example and is not intended to limit the disclosure. Based on the teachings of the disclosure, other structures of the support member 110 adopted by those skilled in the art are all within the protection scope of the disclosure.

In the implementation, the proximal end of the driving shaft 141 has external threads. The mandrel and the driving shaft 141 are connected via threads, so that an axial movement of the driving shaft 141 may be controlled by the mandrel outside the patient's body. It is noted that only part of a structure of the delivery device is illustrated herein, and the rest of the structure of the delivery device may adopt any existing suitable structure, which will not be repeated herein.

Specifically, an outer wall of a proximal end of the support member 110 symmetrically defines at least one snap-fitting opening 114 communicating with a tube cavity of the support member 110. The delivery tube 210 is provided with a connecting member 220 at a distal end thereof. The connecting member 220 includes two branches, and a tail end of each branch is the snap-fitting protrusion 221. In a free state, both branches are adjacent to a central axis of the connecting member 220. During assembly, the connecting member 220 is inserted into the support member 110, and then the mandrel of the delivery device 200 is inserted into the delivery tube 210 until the mandrel is inserted into the connecting member 220 and pushes the two branches of the connecting member 220 outward to drive the snap-fitting protrusion 221 at the tail end of the branch to snap into the snap-fitting opening 114 of the support member 110, such that the support member 110 and the connecting member 220 are connected with each other, that is, the atrioventricular valve clamping device 100 and the delivery device 200 are connected. When the mandrel is withdrawn from the connecting member 220 and the delivery tube 210, the two branches return inward to the free state, and the snap-fitting protrusion 221 is detached from the snap-fitting opening 114 of the support member 110, so that the atrioventricular valve clamping device 100 is disengaged from the delivery device 200. The connecting member 220 may be made from a material with certain hardness and elasticity, such as Nitinol. The delivery tube 210 may have a multi-layer composite tube body. The mandrel may be made from stainless steel or Nitinol.

There is a through-hole inside the support member 110 as the penetrating passage for the driving shaft 141. The driving shaft 141 slidably penetrates in the penetrating passage of the support member 110 in the axial direction (i.e., the Z-direction) and is fixedly connected with the connecting base 142. After the clamping member 130 and the gripping member cooperatively capture the valve leaflet, the driving shaft 141 is driven by the mandrel to move in the Z-direction, so as to drive the clamping arms 131 to fold relative to the support member 110, and make the atrioventricular valve clamping device 100 unfolded below the valve leaflets. And then, a connection between the mandrel and the driving shaft 141 may be released, the mandrel is withdrawn between the two branches of the connecting member 220, and the snap-fitting protrusion 221 is disengaged from the snap-fitting opening 114 of the support member 110, such that the atrioventricular valve clamping device 100 is detached from the delivery device 200.

Refer to FIGS. 21-24 and FIGS. 17-19, the following will take a repair process of the anterior leaflet and septal leaflet of the tricuspid valve as an example to illustrate an operation method of the atrioventricular valve clamping system of the disclosure, which mainly includes the following.

The distal end of the delivery device 200 and the atrioventricular valve clamping device 100 are delivered to the right atrium RA through the inferior vena cava by puncturing a femoral venous. The atrioventricular valve clamping device 100 is then controlled to approach the anterior and septal leaflets of the tricuspid valve TV. The locking portion 170 in the base 160 is unlocked, the mandrel and the driving shaft 141 are pushed to move toward the distal end, the clamping arms 131 are driven to unfold relative to the support member 110 and the occluding member 120, and then a direction of the clamping arms 131 is adjusted, and meanwhile, a position of the clamping arms 131 relative to the anterior and septal leaflets of the tricuspid valve TV may be observed through medical imaging equipment, so that clamping arms 131 are substantially perpendicular to free edges of the anterior and septal leaflets. Then, the atrioventricular valve clamping device 100 is pushed to the right ventricle RV by the delivery device 200 to be below the anterior and septal leaflets, and the two clamping arms 131 is further unfolded to a gripping position. At the same time, each of the gripping arms 151 is controlled to be close to the outer surface of the occluding member 120, and meanwhile, each gripping arm 151 and a corresponding clamping arm 131 cooperate to define a leaflet accommodating space therebetween.

The gripping arms 151 on both sides may be released simultaneously or sequentially, and the two gripping arms 151 cooperate with the two clamping arms 131 to capture the anterior and septal leaflets. And then, the mandrel and the driving shaft 141 are pulled toward the proximal end, thereby driving the two clamping arms 131 to fold, so that the anterior and septal leaflets are clamped between the occluding member 120 and the two clamping arms 131.

Figure 23:
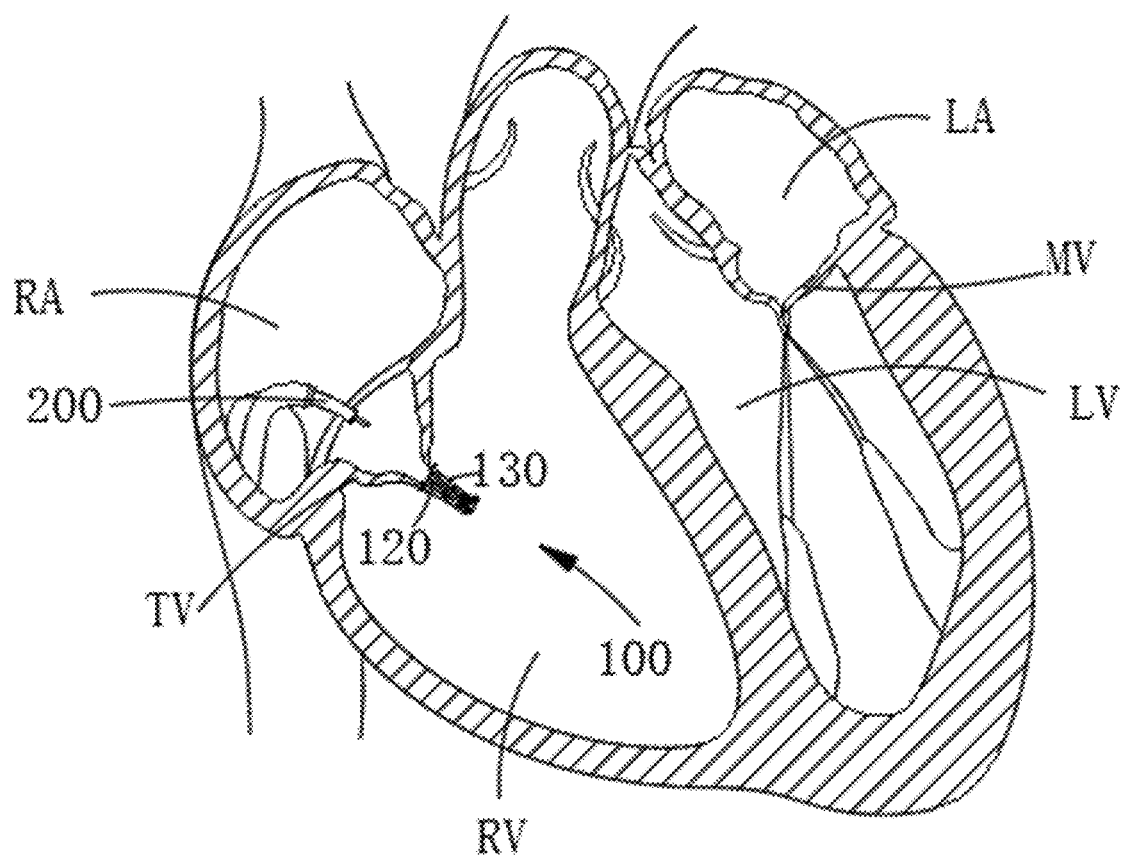
Figure 24:
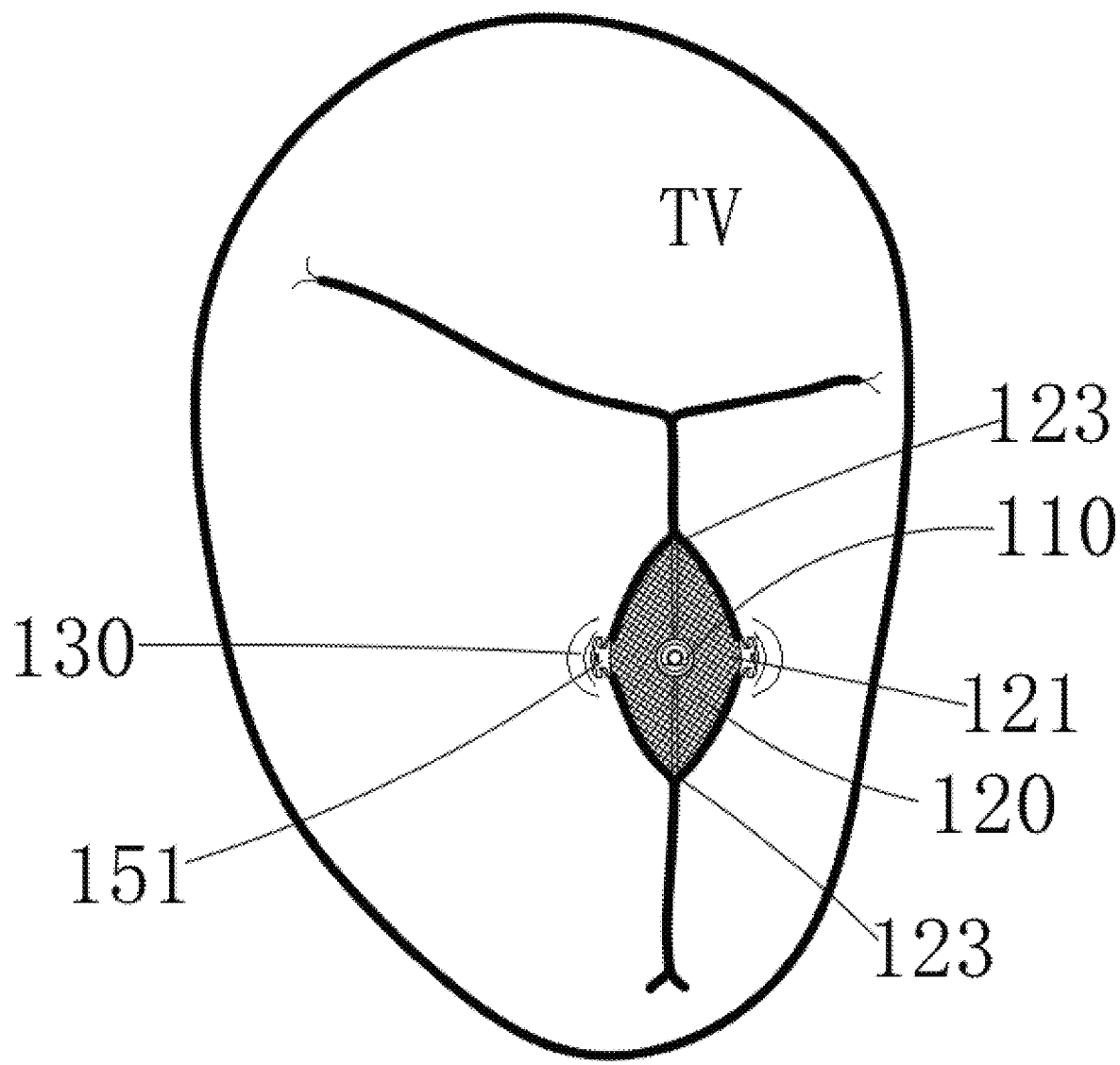
FIG. 24 is a schematic diagram illustrating the adjacent leaflets of the tricuspid valve that has been repaired by the atrioventricular valve clamping device illustrated in FIG. 3.

A threaded connection between the mandrel and the driving shaft 141 is released, and the mandrel is withdrawn, the two branches of the connecting member 220 are restored to a state of being close to each other, the snap-fitting protrusion 221 is detached from the snap-fitting opening 114 of the support member 110, and the atrioventricular valve clamping device 100 is disengaged from the delivery device 200, and then the delivery device 200 is withdrawn from the body, such that an implantation state is achieved, as illustrated in FIG. 23 and FIG. 24, the atrioventricular valve clamping device 100 stretches the anterior leaflet and septal leaflet of the tricuspid valve TV toward each other, completing edge-to-edge repair of the anterior leaflet and the septal leaflet.

After the atrioventricular valve clamping device 100 is implanted, the occluding member 120 with resilience is filled between the clamped anterior and septal leaflets. On the one hand, the gap between the valve leaflets is occluded by the occluding member 120 to reduce regurgitation, and on the other hand, the occluding member 120 provides radial support force for the valve leaflets, and the occluding member 120 has a buffering effect on the pulsating valve leaflets, such that the degree of stretching of on the valve leaflets by the atrioventricular valve clamping device 100 may be adjusted to avoid damage to the valve leaflets.

Figure 25:
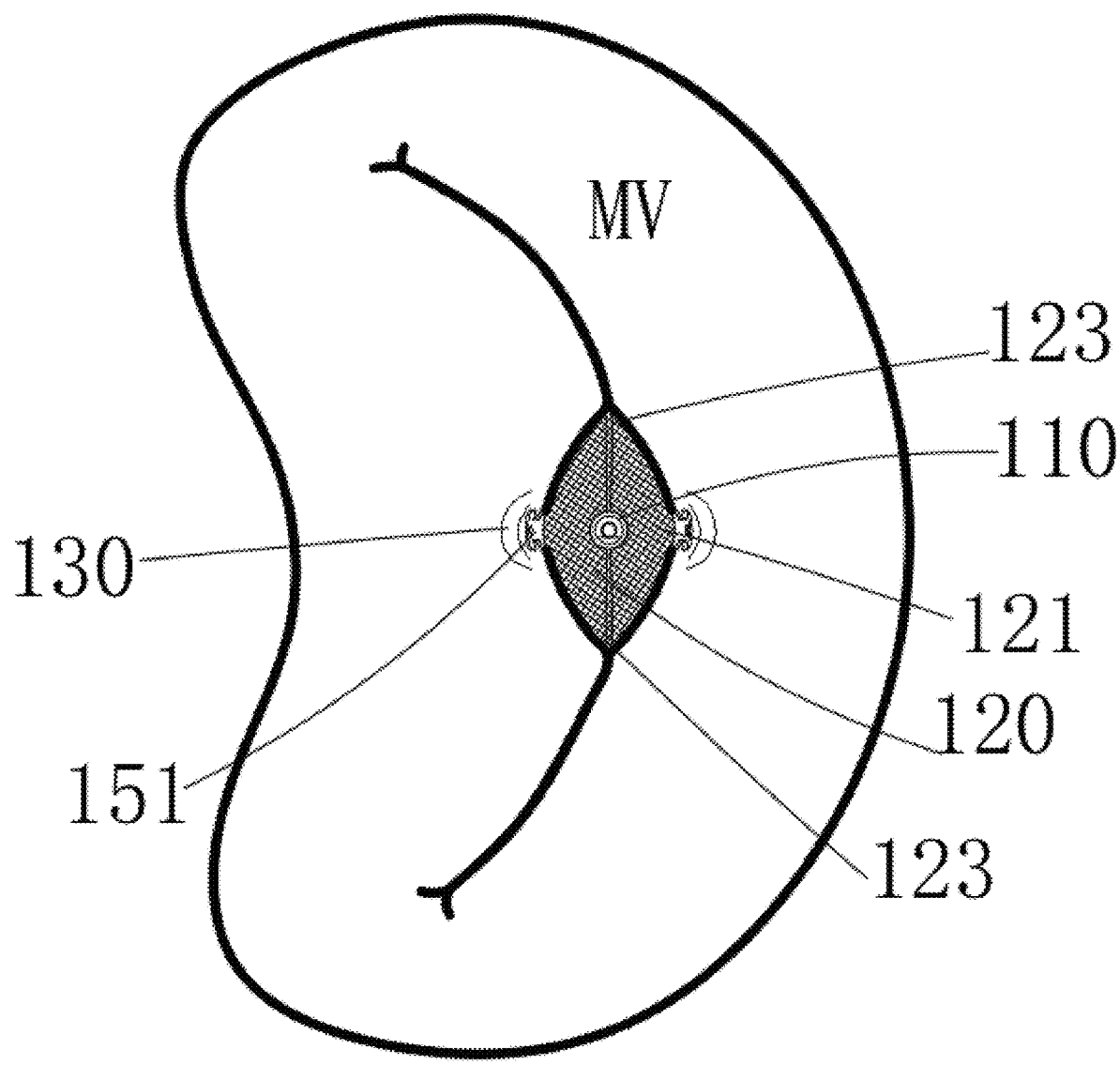
FIG. 25 is a schematic diagram illustrating adjacent valve leaflets of the mitral valve that has been repaired by the atrioventricular valve clamping device illustrated in FIG. 3.

The atrioventricular valve clamping device 100 is suitable for a tricuspid valve clamping operation, and it can also be applied in a mitral valve clamping operation as illustrated in FIG. 25, which has a different intervention path from the tricuspid valve clamping operation. For example, the interventional path of the mitral valve clamping operation may be femoral vein-inferior vena cava-right atrium-atrial septum-left atrium-left ventricle, or may also be a transapical path.

Figure 26:
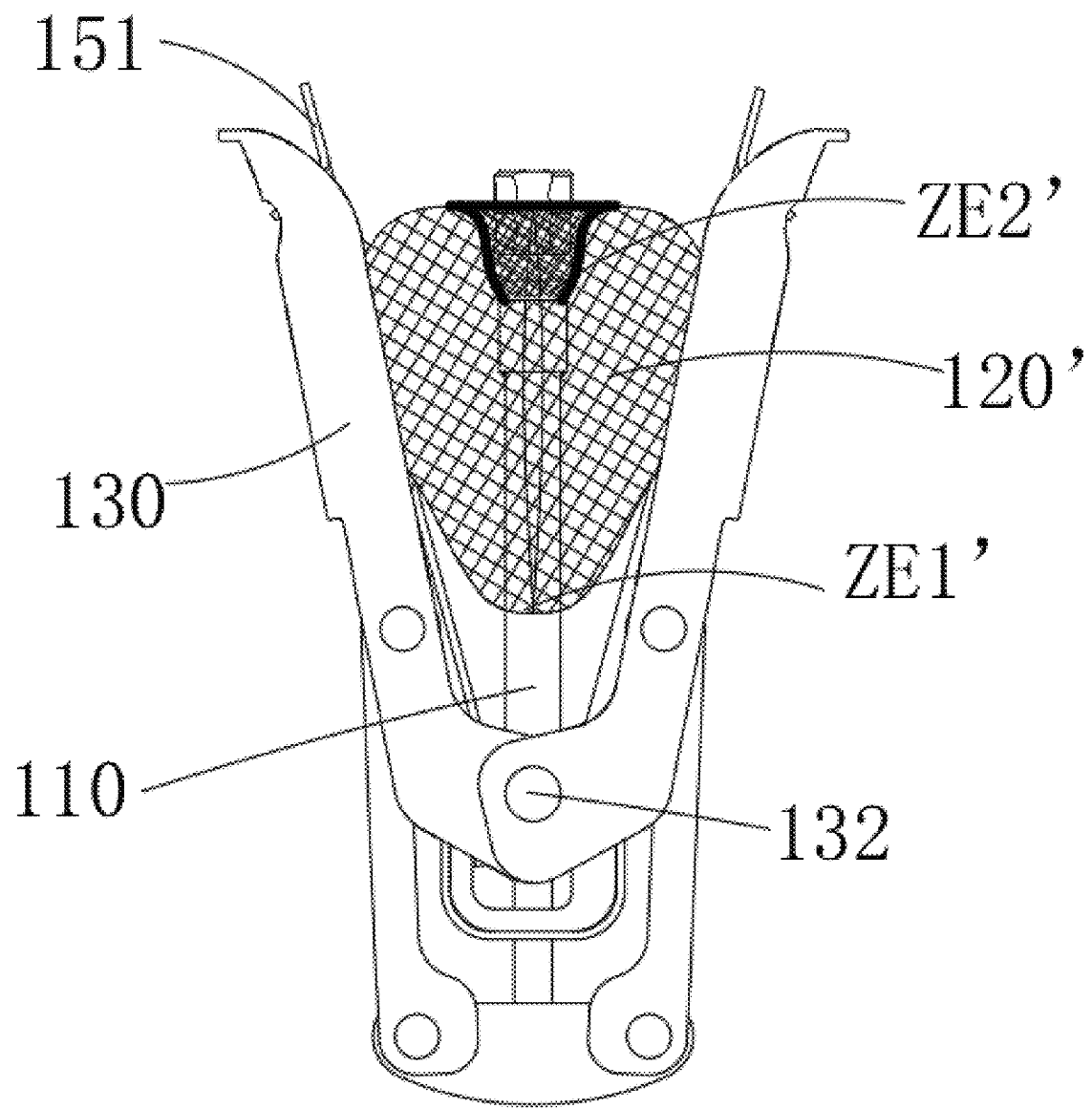
FIG. 26 is a front view of an atrioventricular valve clamping device of an implementation of the disclosure.
Figure 27:
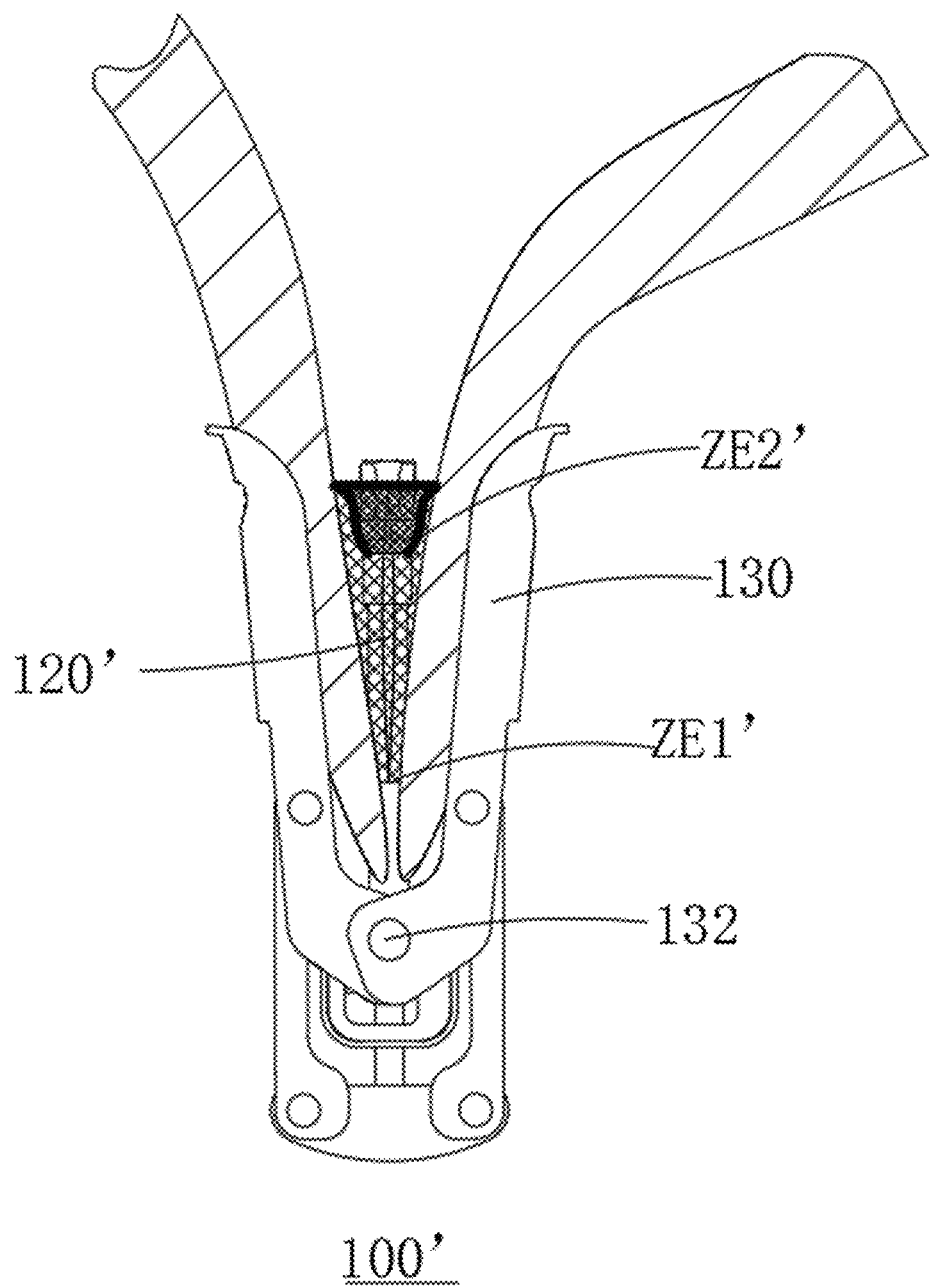
FIG. 27 is a front view of the atrioventricular valve clamping device illustrated in FIG. 26 when clamping valve leaflets.

Refer to FIG. 26 and FIG. 27, in the atrioventricular valve clamping device 100' provided in an implementation of the disclosure, the support member 110, the clamping member 130, the driving member, the gripping member, the occluding member 120', and the like are the same in structure as that in the atrioventricular valve clamping device 100 illustrated in FIG. 3, which are not repeated herein, except that an assembly relationship between the occluding member 120' and the support member 110 is changed.

In this implementation, the first Z-direction end-portion ZE1' of the occluding member 120' close to the pivot point 132 is movably sleeved on the support member 110, and the second Z-direction end-portion ZE2' of the occluding member 120' away from the pivot point 132 is fixedly connected with the support member 110.

Specifically, the second Z-direction end-portion ZE2' is fixedly connected (for example, welded) with a sleeve, and the sleeve is fixedly connected (for example, welded) with the support member 110. The first Z-direction end-portion ZE1' defines a through-hole that has a bound-off edge, and the first Z-direction end-portion ZE1' is movably sleeved on the distal end of the support member 110 through the through-hole.

In the folded state of the atrioventricular valve clamping device 100', that is, when the valve leaflets are clamped between the occluding member 120' and the clamping member 130, due to the second Z-direction end-portion ZE2' is fixedly connected with the support member 110, and the first Z-direction end-portion ZE1' is movably sleeved on the distal end of the support member 110, and thus the first Z-direction end-portion ZE1' of the occluding member 120' may extend in the Z-direction toward edges of the valve leaflets under an clamping action of the clamping member 130, thereby also allowing the occluding member 120' to be significantly deformed in the Z-direction to better adapt to the shapes or forms of the valve leaflets and increase the fit area between the valve leaflets and the occluding member 120'.

Figure 28:
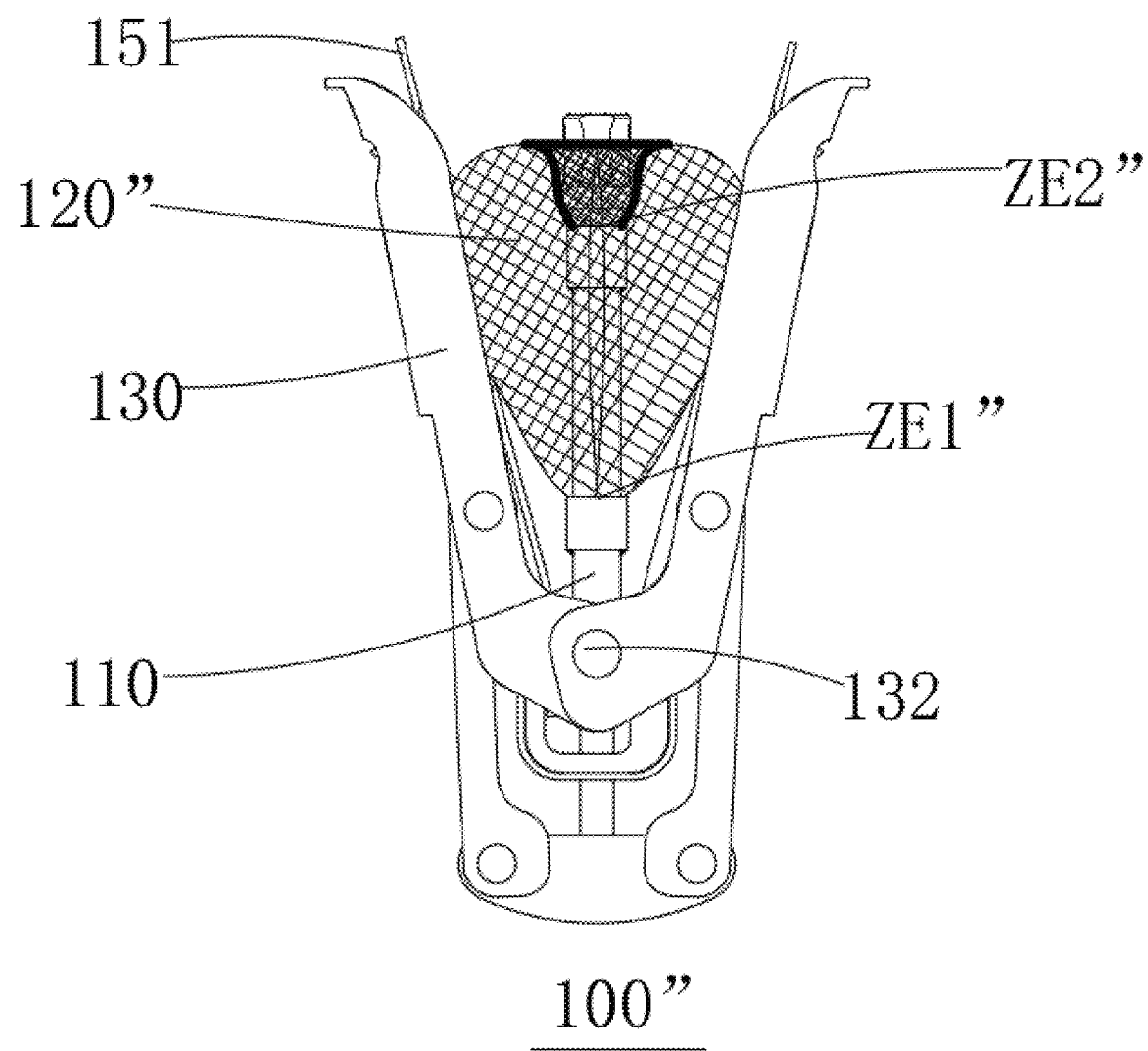
FIG. 28 is a front view of an atrioventricular valve clamping device of an implementation of the disclosure.
Figure 29:
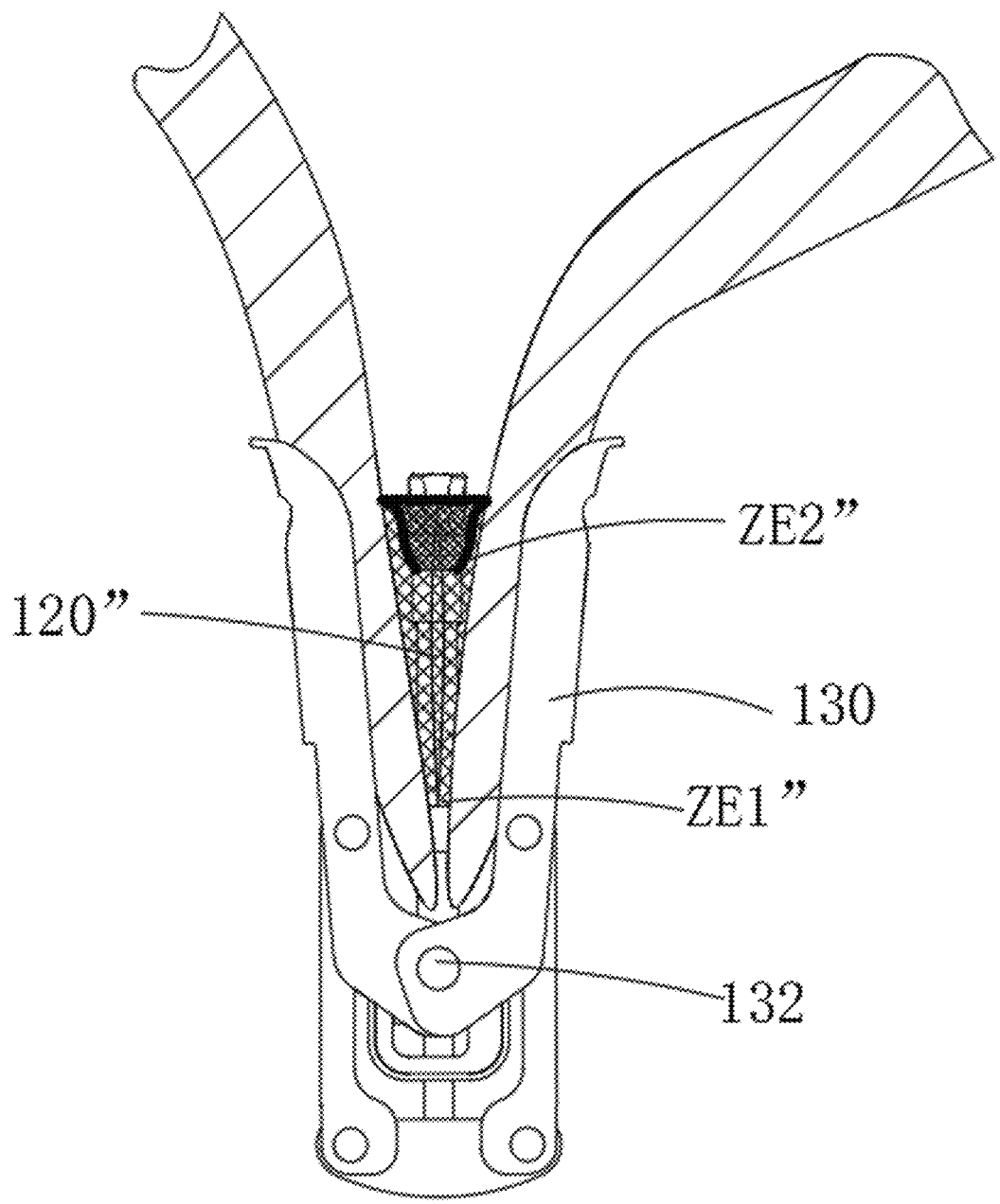
FIG. 29 is a front view of the atrioventricular valve clamping device illustrated in FIG. 28 when clamping valve leaflets.

Refer to FIG. 28 and FIG. 29, in the atrioventricular valve clamping device 100" provided in an implementation of the disclosure, the support member 110, the clamping member 130, the driving member, the gripping member, the occluding member 120", and the like are the same in structure as that in the atrioventricular valve clamping device 100 illustrated in FIG. 3, which are not repeated herein, except that an assembly relationship between the occluding member 120" and the support member 110 is changed.

In this implementation, the first Z-direction end-portion ZE1" of the occluding member 120" close to the pivot point 132 is fixedly connected with the support member 110. The second Z-direction end-portion ZE2" of the occluding member 120" away from the pivot point 132 is also fixedly connected with the support member 110.

Specifically, the second Z-direction end-portion ZE2″ is fixedly connected (for example, welded) with a sleeve, and the sleeve is fixedly connected (for example, welded) with the support member 110. The first Z-direction end-portion ZE1″ is fixedly connected (for example, welded) with another sleeve, and the another sleeve is fixedly connected (for example, welded) with the support member 110.

In the folded state of the atrioventricular valve clamping device 100″, that is, when the valve leaflets are clamped between the occluding member 120″ and the clamping member 130, due to the second Z-direction end-portion ZE2″ and the first Z-direction end-portion ZE1″ are both fixedly connected with the support member 110, both the second Z-direction end-portion ZE2″ and the first Z-direction end-portion ZE1″ of the occluding member 120″ cannot be deformed in the Z-direction under the clamping action of the clamping member 130, but may be significantly deformed in the X-direction and the Y-direction to provide a more stable support for the valve leaflets.

Figure 30:
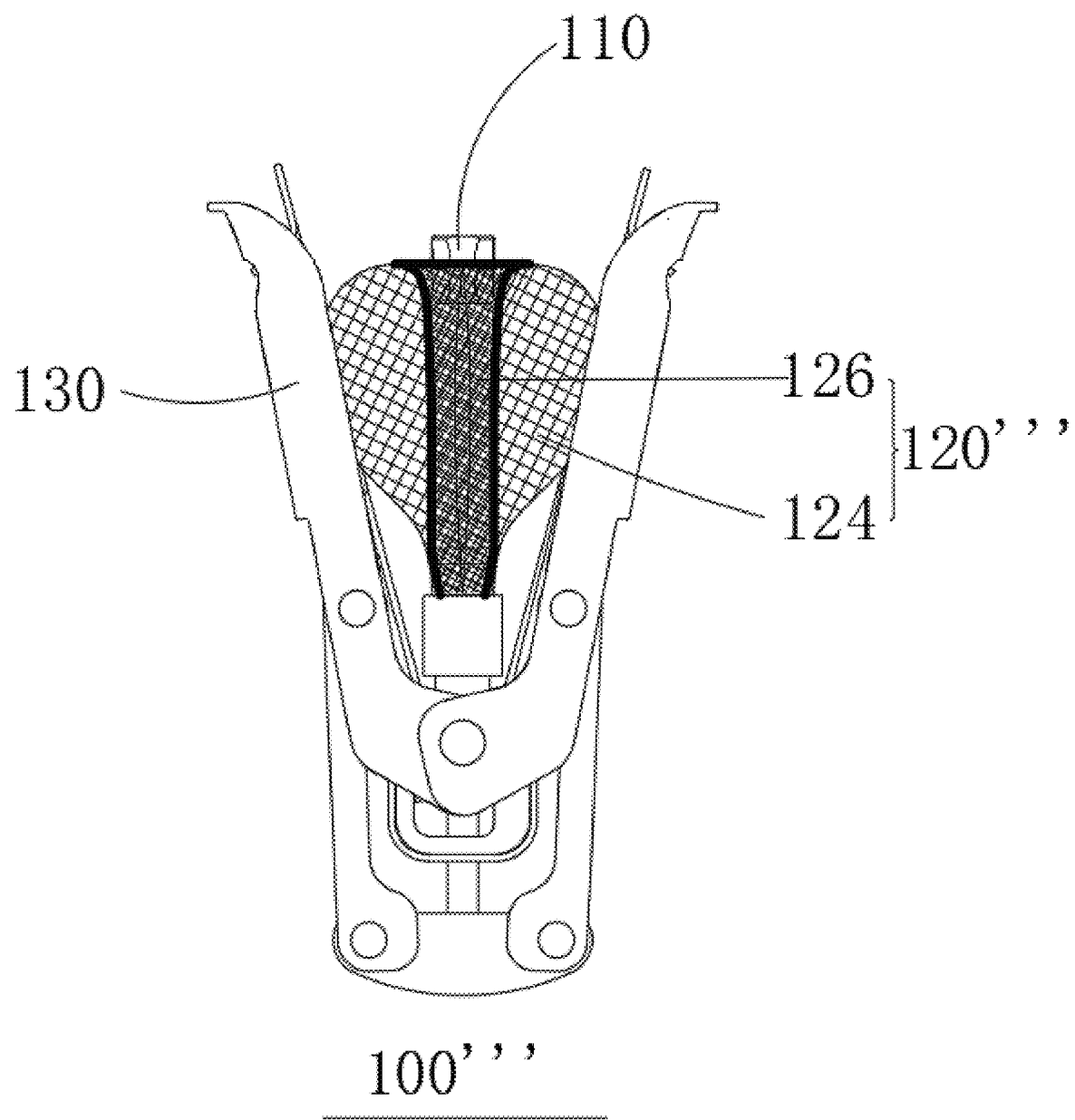
FIG. 30 is a front view of an atrioventricular valve clamping device of an implementation of the disclosure.
Figure 31:
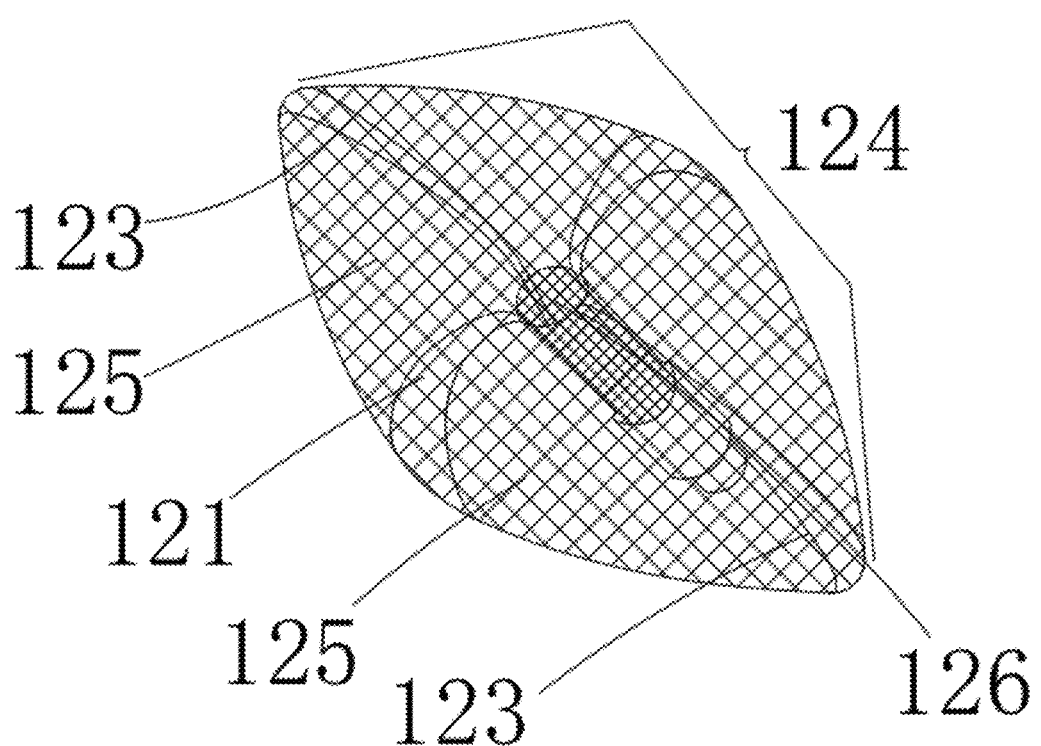
FIG. 31 is a schematic structural diagram of an occluding member illustrated in FIG. 30.
Figure 32:
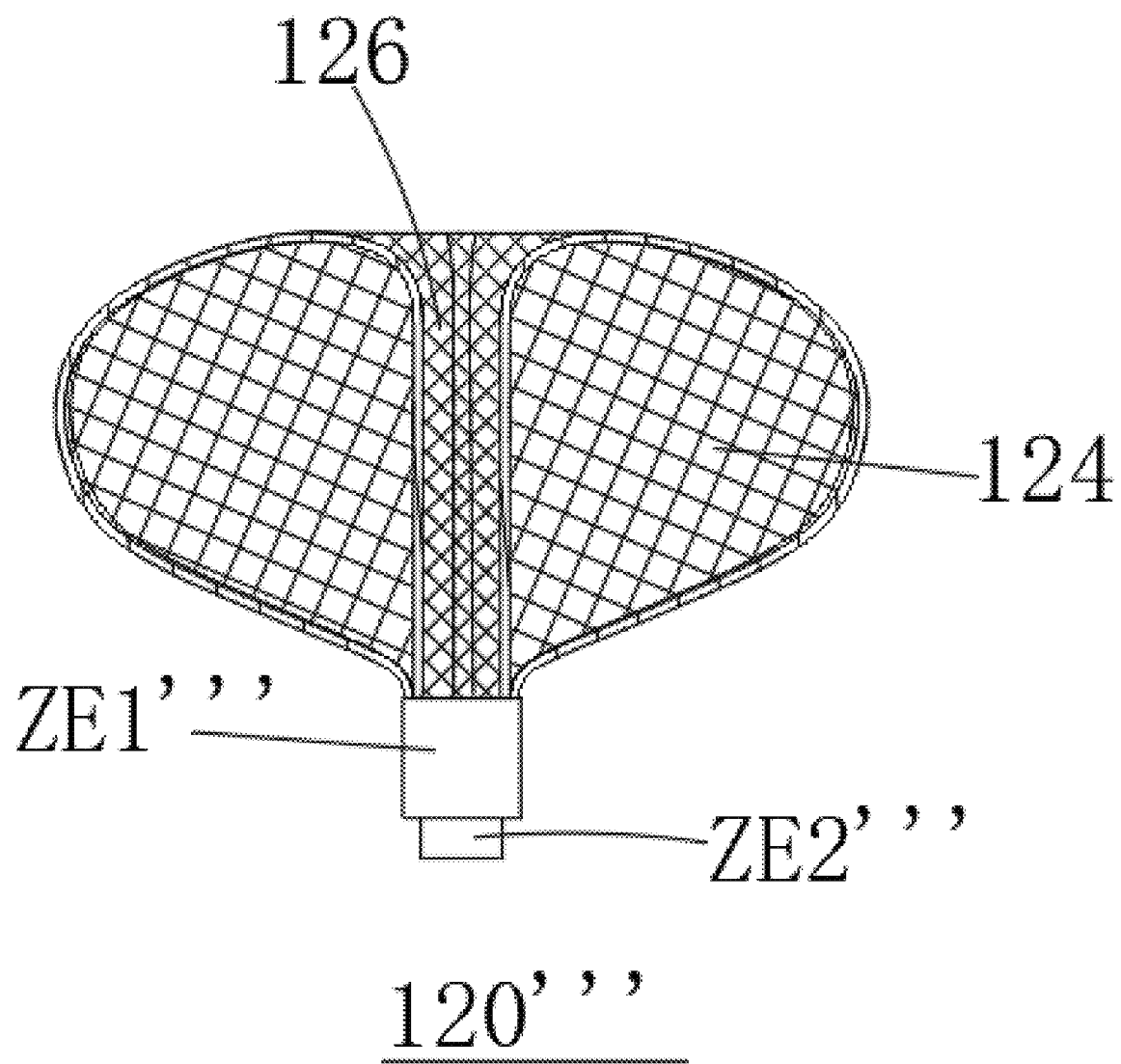
FIG. 32 is a schematic cross-sectional structural diagram of the occluding member illustrated in FIG. 30.

Refer to FIG. 30 to FIG. 32, in the atrioventricular valve clamping device 100‴ provided in an implementation of the disclosure, the support member 110, the clamping member 130, the driving member, the gripping member, and the like are the same in structure as that in the atrioventricular valve clamping device 100 illustrated in FIG. 3, which are not repeated herein, except that a structure of the occluding member 120‴ itself and an assembly relationship between the occluding member 120‴ and the support member 110 are changed.

In the implementation, the occluding member 120‴ includes an outer body portion 124 and an inner cylindrical portion 126 inside the outer body portion 124. The clamping-supporting portion 121, the end portion 123, and the first transition portion 125 are arranged on the outer body portion 124. The first Z-direction end-portion ZE1‴ of the occluding member 120‴ is fixedly connected with the support member 110, the second Z-direction end-portion ZE2‴ is fixedly connected with the support member 110, and the first Z-direction end-portion ZE1‴ is fixedly sleeved outside the second Z-direction end-portion ZE2‴. The inner cylindrical portion 126 extends, toward the proximal end in the Z-direction, from the second Z-direction end-portion ZE2‴ to be connected with the outer body portion 124.

Specifically, the second Z-direction end-portion ZE2‴ is fixedly connected (for example, welded) with a first sleeve, the first sleeve is fixedly connected (for example, welded) with the support member 110, and the support member 110 extends through the inner cylindrical portion 126 and the first sleeve in the Z-direction. The first Z-direction end-portion ZE1‴ is fixedly connected (for example, welded) with a second sleeve, and the second sleeve is fixedly connected (for example, welded) with the first sleeve.

Due to the existence of the inner cylindrical portion 126, the occluding member 120‴ has a double-layer structure. In the folded state of the atrioventricular valve clamping device 100‴, the valve leaflets are clamped between the occluding member 120‴ and the clamping member 130, and the occluding member 120‴ having the double-layer structure may provide a larger and more stable clamping force for the valve leaflets.

Figure 33:
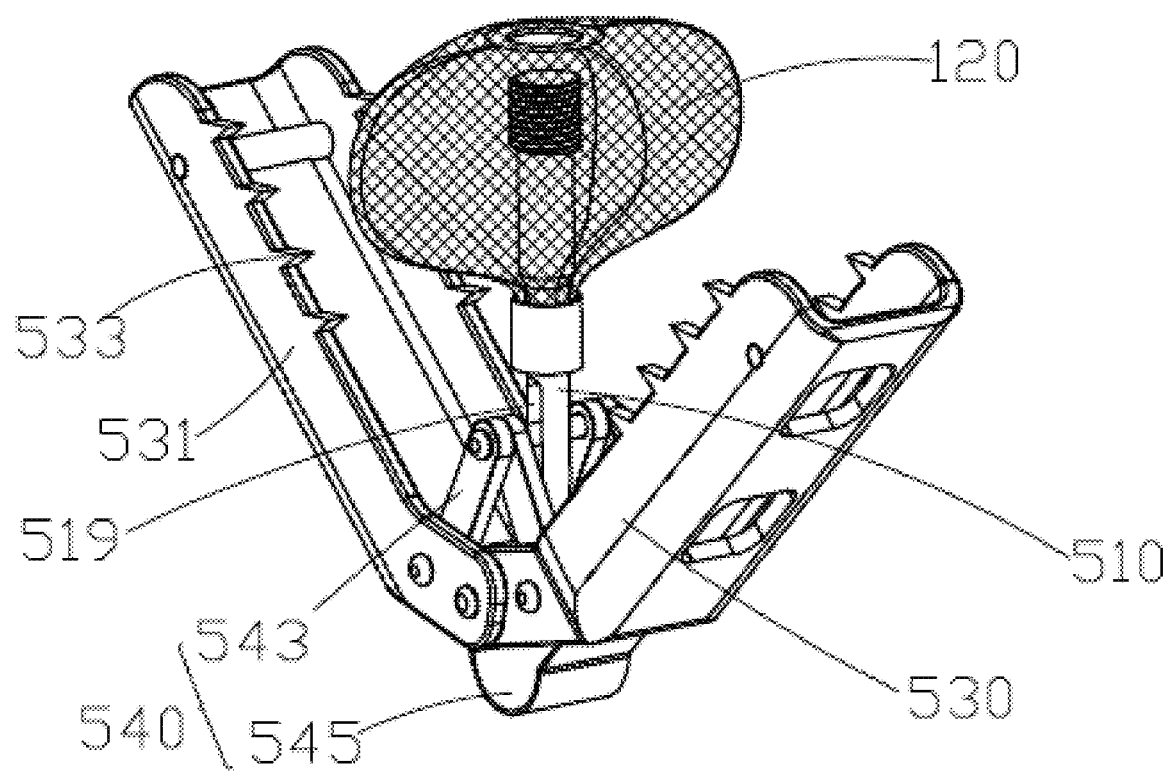
FIGS. 33 and 34 are respectively a schematic perspective structural diagram and a front view of an atrioventricular valve clamping device of an implementation of the disclosure.
Figure 34:
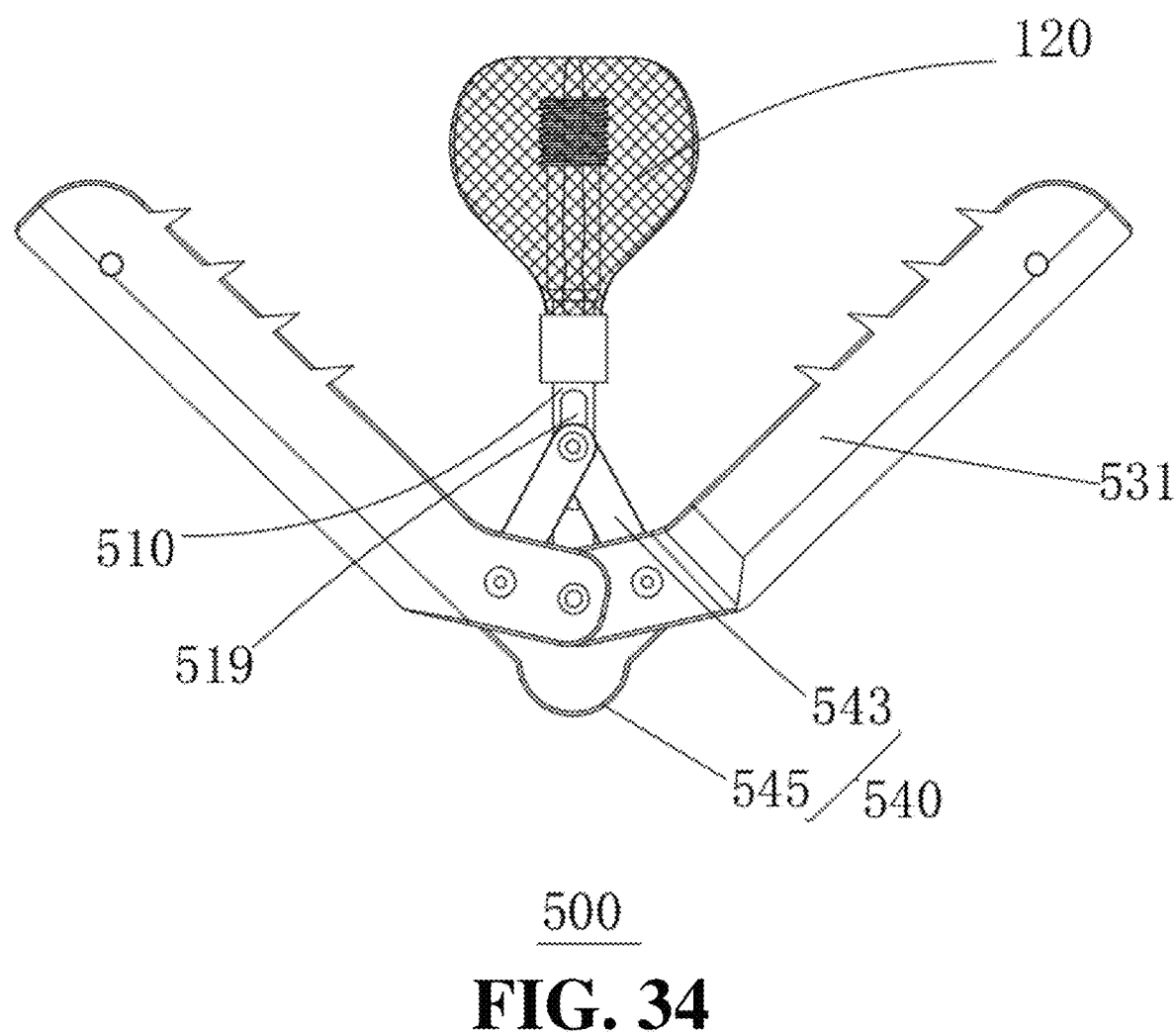

Refer to FIG. 33 and FIG. 34, compared with the atrioventricular valve clamping device 100 illustrated in FIG. 3, in an atrioventricular valve clamping device 500 illustrated in FIG. 33 and FIG. 34, the occluding member 120 remains unchanged in structure, which will not be repeated herein, but a support member 510, a clamping member 530, and a driving member 540 are changed in structure.

Specifically, in this implementation, the clamping member 530 includes a set of clamping arms 531, and each clamping arm 531 is provided with at least one anchoring member 533. When the clamping arms 531 are folded relative to the occluding member 120, the anchoring member 533 may abut against the valve leaflet to be embedded in meshes of the occluding member 120 of a mesh structure, such that valve leaflet issue may be retained by the anchoring member 533 on the basis that the occluding member 120 and the clamping arm 531 clamp the valve leaflets.

The driving member 540 includes a driving shaft (not illustrated), an automatic folding unit 545, and at least two connecting rods 543. In an implementation, each of the connecting rods 543 has one end rotatably connected with a corresponding clamping arm 531 and the other end directly rotatably connected with the driving shaft via a pin shaft. The driving shaft movably penetrates the support member 510. The automatic folding unit 545 connects the two clamping arms 531 for making the clamping member 530 abut against the occluding member 120 in the free state.

A base (not illustrated) is integrally formed with a distal end of the support member 510. The two clamping arms 531 are rotatably connected with the base. The support member 510 defines an axial groove 519 for the pin shaft to extend through. When the driving shaft drives the pin shaft to move in the axial groove 519 toward the distal end of the support member 510, the connecting rods 543 are driven to overcome resistance of the automatic folding unit 545 to make the two clamping arms 531 unfolded.

In the implementation, the automatic folding unit 545 is a U-shaped resilient piece. Both ends of the U-shaped resilient piece are respectively connected with the clamping arms 531. When the driving shaft does not push the pin shaft, the U-shaped resilient piece restores to drive the two clamping arms 531 to fold and abut against the occluding member 120. It may be understood that, in other implementations, the automatic folding unit 545 may also be a resilient member such as a V-shaped resilient sheet or a torsion spring.

Figure 35:
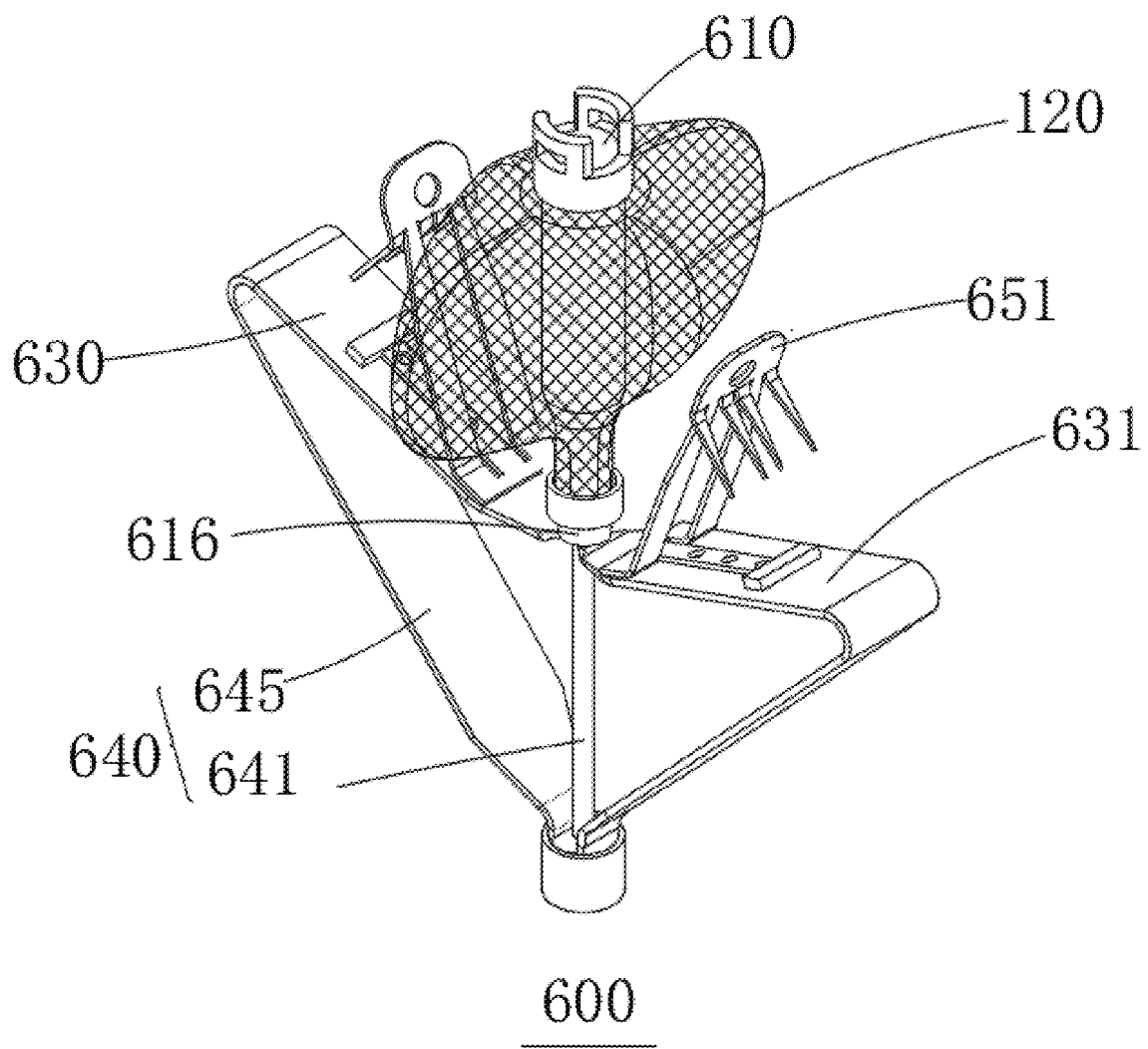
FIGS. 35 and 36 are respectively a schematic perspective structural diagram and a front view of an atrioventricular valve clamping device of an implementation of the disclosure.
Figure 36:
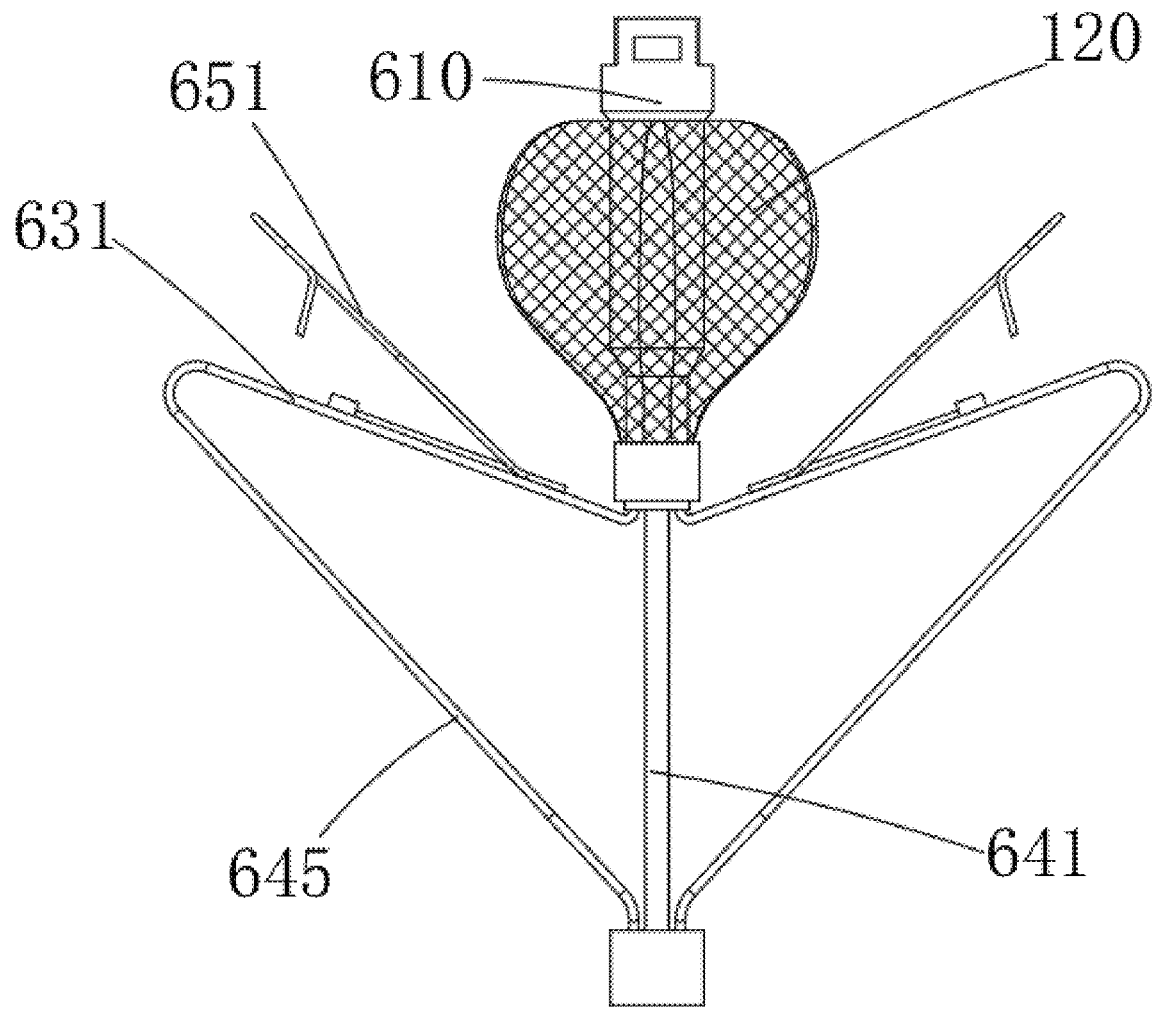

Refer to FIG. 35 and FIG. 36, compared with the atrioventricular valve clamping device 100 illustrated in FIG. 3, in an atrioventricular valve clamping device 600 illustrated in FIG. 35 and FIG. 36, the occluding member 120 remains unchanged in structure, which will not be repeated herein, but a clamping member 630, a driving member 640, and the like are changed in structure.

In the implementation, a base 616 is integrally formed with a distal end of the support member 610. The clamping arm 631 of the clamping member 630 has one end connected with the base 616. The driving member 640 includes a driving shaft 641 and at least two resilient driving arms 645. Each of the resilient driving arms 645 has one end fixedly connected with one end of the driving shaft 641 and the other end connected with the other end of the clamping arm 631. The other end of the driving shaft 641 movably penetrates the support member 610. The resilient driving arms 645 are configured to make the clamping member 630 abut against the occluding member 120 in the free state. Each of gripping arms 651 has one end connected with the clamping arm 631 of the clamping member 630, and in the unfolded state of the atrioventricular valve clamping device 600, the gripping arms 651 may be controlled to unfold relative to the clamping arms 631, allowing the valve leaflets to enter between the gripping arm 651 and the clamping arms 631.

In the implementation, the two clamping arms 631 are integrally formed with the two resilient driving arms 645.

That is, the two clamping arms 631 themselves are resilient. When the driving shaft 641 moves toward the distal end of the support member 610, the two clamping arms 631 are relatively unfolded by overcoming resistance of the two resilient driving arms 645. When the driving shaft 641 does not push the resilient driving arms 645, the two resilient driving arms 645 restore to drive the two clamping arms 631 to fold and abut against the occluding member 120. It is noted that, when the driving shaft 641 is further pushed toward the distal end of the support member 610, connections between the clamping arms 631 and the resilient driving arms 645 may be gradually moved toward the driving shaft 641 until the clamping arms 631 and the resilient driving arms 645 are substantially in a straight line, and then the gripping arm 651 is controlled to closely contact with the occluding member 120, and in this state, it is easier to retract the entire atrioventricular valve clamping device 600 flattened into the delivery tube.

In addition, the atrioventricular valve clamping device 600 in the implementation can realize a dynamic balance in a valve leaflet clamping state. When the valve leaflets exert a large stretching force on the atrioventricular valve clamping device 600, the resilient driving arms 645 and the clamping arms 631 can adjust a clamping angle within a certain range without being detached from the valve leaflets, preventing the valve leaflets from being damaged by an excessive stretching force.

It may be understood that, the valve clamping system provided in the disclosure may include any one of the atrioventricular valve clamping devices described above and the delivery device capable of delivering the atrioventricular valve clamping device from an outside of the body to the position near the tricuspid or mitral valve and clamping the valve leaflets.

The foregoing are only exemplary implementations of the disclosure that enable those skilled in the art to appreciate or achieve the disclosure. Various modifications to these implementations will be readily apparent to those skilled in the art, and generic principles defined herein may be implemented in other implementations without departing from the spirit or scope of the disclosure. Thus, the disclosure will not to be limited to the implementations referred to herein, but will be subjected to the broadest scope consistent with the principles and novel features claimed herein.

What is claimed is:

1. An atrioventricular valve clamping device, comprising a support member, an occluding member, and a clamping member, wherein
    a direction of a central axis of the occluding member is regarded as a Z-direction, a direction parallel to a width direction of the clamping member and perpendicular to the Z-direction is regarded as a Y-direction, and a direction perpendicular to the Y-direction and the Z-direction is regarded as an X-direction;
    the support member has a length in the Z-direction, the occluding member is sleeved on the support member in the Z-direction, and the clamping member is disposed outside the occluding member and configured to be unfolded or folded relative to the occluding member;
    the occluding member is resilient and has a three-dimensional shape;
    the occluding member comprises two clamping-supporting portions opposite each other in the X-direction, two end portions opposite each other in the Y-direction, and first transition portions each for transition connection between the clamping-supporting portion and the end portion; and
    on an X-Y plane, an outer contour of each of the two end portions forms a pointed end extending outward in the Y-direction, wherein the pointed end represents that the end portion is pointed or tend to be pointed, and the end portion at least partially extends beyond the clamping member in the Y-direction.

2. The atrioventricular valve clamping device of claim 1, wherein a maximum value among distances between each two opposite parts of the two clamping-supporting portions in the X-direction is less than a maximum value among distances between each two opposite parts of the two end portions in the Y-direction, and the two end portions are sharper than the two clamping-supporting portions.

3. The atrioventricular valve clamping device of claim 1, wherein on the X-Y plane, the two clamping-supporting portions have an outer contour substantially in the shape of two opposite arcs that are convex outward, and the two end portions have an outer contour substantially in the shape forming by V-shape and inverted V-shape opposite each other.

4. The atrioventricular valve clamping device of claim 3, wherein each of the two clamping-supporting portions comprises a first segment and a second segment opposite each other in the Y-direction, and each of the two end portions comprises a third segment and a fourth segment opposite each other in the X-direction; distances between each two opposite parts of the two clamping-supporting portions in the X-direction are greater than distances between each two opposite parts of the third segment and the fourth segment in the X-direction; and distances between each two opposite parts of the two end portions in the Y-direction are greater than distances between each two opposite parts of the first segment and the second segment in the Y-direction.

5. The atrioventricular valve clamping device of claim 4, wherein the first transition portion comprises a fifth segment and a sixth segment opposite each other in the X-direction; and in the Y-direction from a Y-direction middle-segment of the occluding member to the end portion, the distances between each two opposite parts of the two clamping-supporting portions in the X-direction gradually decrease, the distances between each two opposite parts of the fifth segment and the sixth segment in the X-direction gradually decrease, and the distances between each two opposite parts of the third segment and the fourth segment in the X-direction gradually decrease.

6. The atrioventricular valve clamping device of claim 4, wherein on the X-Y plane, a second transition portion in the shape of an arc that is convex outward is connected between the third segment and the fourth segment, and the second transition portion has a radius ranging from 0.005 mm to 5 mm.

7. The atrioventricular valve clamping device of claim 1, wherein on the X-Y plane, the occluding member has an outer contour in the shape of oval, fusiform, or substantial rhombus, and the outer contour in the shape of oval, fusiform, or substantial rhombus has a short axis in the X-direction and a long axis in the Y-direction.

8. The atrioventricular valve clamping device of claim 7, wherein the occluding member comprises a first Z-direction end-portion and a second Z-direction end-portion; the outer contour of the occluding member on the X-Y plane gradually increases from the second Z-direction end-portion to a Z-direction middle-segment of the occluding member; and the outer contour of the occluding member on the X-Y plane gradually reduces from the Z-direction middle-segment to the first Z-direction end-portion of the occluding member.

9. The atrioventricular valve clamping device of claim 8, wherein on a Y-Z plane, the outer contour of the occluding member is substantially in the shape of a capsule, a racetrack, or a water-drop, and an outer contour of the two end portions forms two first arc-shaped segments that are convex outward.

10. The atrioventricular valve clamping device of claim 8, wherein on an X-Z plane, the outer contour of the occluding member is substantially in the shape of a water-drop, and an outer contour of the two clamping-supporting portions forms two second arc-shaped segments that are convex outward.

11. The atrioventricular valve clamping device of claim 1, wherein the occluding member is a three-dimensional mesh structure made from a shape memory material.

12. The atrioventricular valve clamping device of claim 11, wherein the three-dimensional mesh structure is covered with a biocompatible film at an outside and/or an inside of the three-dimensional mesh structure.

13. The atrioventricular valve clamping device of claim 1, wherein the clamping member is rotatably connected with the support member at a pivot point, and configured to be radially unfolded or folded about the pivot point; and the occluding member comprises a first Z-direction end-portion and a second Z-direction end-portion, and at least one of the first Z-direction end-portion or the second Z-direction end-portion is fixedly connected with the support member.

14. The atrioventricular valve clamping device of claim 13, wherein
the first Z-direction end-portion of the occluding member is fixedly connected with the support member, the second Z-direction end-portion is a free end or movably sleeved on the support member, and the first Z-direction end-portion is closer to the pivot point than the second Z-direction end-portion; or
the first Z-direction end-portion of the occluding member is movably sleeved on the support member, the second Z-direction end-portion is fixedly connected with the support member, and the first Z-direction end-portion is closer to the pivot point than the second Z-direction end-portion; or
the first Z-direction end-portion of the occluding member is fixedly connected with the support member, the second Z-direction end-portion is fixedly connected with the support member, and the first Z-direction end-portion is closer to the pivot point than the second Z-direction end-portion.

15. The atrioventricular valve clamping device of claim 14, wherein the occluding member is hollow, one of the first Z-direction end-portion or the second Z-direction end-portion that is not fixedly connected with the support member defines a through-hole having a bound off edge.

16. The atrioventricular valve clamping device of claim 1, wherein:
the clamping member is connected with the support member at a pivot point, and the clamping member is configured to be radially unfolded or folded about the pivot point;
the occluding member comprises a first Z-direction end-portion and a second Z-direction end-portion, and the first Z-direction end-portion is closer to the pivot point than the second Z-direction end-portion; and
the first Z-direction end-portion is movably connected with part of the support member within a range smaller than the length of the support member in the Z-direction.

17. The atrioventricular valve clamping device of claim 11, wherein the three-dimensional mesh structure is formed by interweaving a plurality of first wires and a plurality of second wires, and the Z-direction middle-segment of the three-dimensional mesh structure has a greater mesh density than the rest of the three-dimensional mesh structure.

18. The atrioventricular valve clamping device of claim 1, further comprising a driving member, wherein the clamping member comprises two clamping arms symmetrically arranged relative to the occluding member, and the driving member is connected with each of the two clamping arms to drive each of the two clamping arms to move toward or away from the occluding member.

19. The atrioventricular valve clamping device of claim 18, further comprising a gripping member disposed between the clamping member and the occluding member, wherein the gripping member is configured to be unfolded to be away from the occluding member or configured to be folded to approach the occluding member.

20. A valve clamping system, comprising an atrioventricular valve clamping device and a delivery device, wherein
the atrioventricular valve clamping device comprises a support member, an occluding member, and a clamping member, wherein
a direction of a central axis of the occluding member is regarded as a Z-direction, a direction parallel to a width direction of the clamping member and perpendicular to the Z-direction is regarded as a Y-direction, and a direction perpendicular to the Y-direction and the Z-direction is regarded as an X-direction;
the support member has a length in the Z-direction, the occluding member is sleeved on the support member in the Z-direction, and the clamping member is disposed outside the occluding member and configured to be unfolded or folded relative to the occluding member;
the occluding member is resilient and has a three-dimensional shape;
the occluding member comprises two clamping-supporting portions opposite each other in the X-direction, two end portions opposite each other in the Y-direction, and first transition portions each for transition connection between the clamping-supporting portion and the end portion; and
on an X-Y plane, an outer contour of each of the two end portions forms a pointed end extending outward in the Y-direction, wherein the pointed end represents that the end portion is pointed or tend to be pointed, and the end portion at least partially extends beyond the clamping member in the Y-direction; and
the delivery device comprises a delivery tube having an axial length and a mandrel movably inserted in the delivery tube, the delivery tube is detachably connected with the support member, and the mandrel is configured to drive the clamping member to be unfolded or folded.

* * * * *